(12) United States Patent
Xiao et al.

(10) Patent No.: US 10,561,761 B2
(45) Date of Patent: Feb. 18, 2020

(54) POLYMER METAL-ORGANIC FRAMEWORK COMPOSITES

(71) Applicant: Northwestern University, Evanston, IL (US)

(72) Inventors: Jisheng Xiao, Chicago, IL (US); Guillermo A. Ameer, Chicago, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 15/537,054

(22) PCT Filed: Dec. 18, 2015

(86) PCT No.: PCT/US2015/066731
§ 371 (c)(1),
(2) Date: Jun. 16, 2017

(87) PCT Pub. No.: WO2016/100847
PCT Pub. Date: Jun. 23, 2016

(65) Prior Publication Data
US 2018/0236122 A1 Aug. 23, 2018

Related U.S. Application Data

(60) Provisional application No. 62/094,971, filed on Dec. 20, 2014.

(51) Int. Cl.
| | | |
|---|---|---|
| A61L 15/26 | (2006.01) | |
| A61K 31/555 | (2006.01) | |
| A61L 15/44 | (2006.01) | |
| A61P 17/02 | (2006.01) | |
| A61K 47/34 | (2017.01) | |

(Continued)

(52) U.S. Cl.
CPC ............ *A61L 15/26* (2013.01); *A61K 31/555* (2013.01); *A61K 47/34* (2013.01); *A61L 15/20* (2013.01); *A61L 15/42* (2013.01); *A61L 15/425* (2013.01); *A61L 15/44* (2013.01); *A61P 17/02* (2018.01); *A61L 2300/102* (2013.01); *A61L 2300/412* (2013.01); *A61L 2400/12* (2013.01); *A61L 2420/00* (2013.01)

(58) Field of Classification Search
None
See application file for complete search history.

(56) References Cited

U.S. PATENT DOCUMENTS

| | | |
|---|---|---|
| 3,779,242 A | 12/1973 | McCullough |
| 4,399,816 A | 8/1983 | Spangler |

(Continued)

OTHER PUBLICATIONS

Amna et al., Virgin olive oil blended polyurethane micro/nanofibers ornamented with copper oxide nanocrystals for biomedical applications, Int J Nanomedicine. Feb. 13, 2014;9:891-8.

(Continued)

*Primary Examiner* — Aradhana Sasan
(74) *Attorney, Agent, or Firm* — Casimir Jones SC; David W. Staple

(57) ABSTRACT

Provided herein are polymer and metal organic frameworks (MOFs) composites, and methods of use and preparation thereof. In particular, Poly(polyethyleneglycol citrate-co-N-isopropylacrylamide) (PPCN) and copper MOF composites are provided.

17 Claims, 25 Drawing Sheets

(51) Int. Cl.
  A61L 15/20     (2006.01)
  A61L 15/42     (2006.01)

(56) References Cited

U.S. PATENT DOCUMENTS

| | | |
|---|---|---|
| 4,709,695 A | 12/1987 | Kohn et al. |
| 4,732,146 A | 3/1988 | Fasline et al. |
| 4,907,579 A | 3/1990 | Kum |
| 4,909,243 A | 3/1990 | Frank et al. |
| 4,917,112 A | 4/1990 | Kalt |
| 4,926,883 A | 5/1990 | Strock |
| 5,086,763 A | 2/1992 | Hathman |
| 5,167,613 A | 12/1992 | Karami et al. |
| 7,750,201 B2 | 7/2010 | Patel et al. |
| 8,404,264 B2 | 3/2013 | Ameer et al. |
| 8,431,151 B2 | 4/2013 | Mather et al. |
| 8,568,765 B2 | 10/2013 | Ameer et al. |
| 8,580,912 B2 | 11/2013 | Ameer et al. |
| 8,758,796 B2 | 6/2014 | Ameer et al. |
| 8,772,437 B2 | 7/2014 | Ameer et al. |
| 8,778,387 B2 | 7/2014 | Tennican et al. |
| 8,865,143 B2 | 10/2014 | Lu et al. |
| 8,911,720 B2 | 12/2014 | Ameer et al. |
| 2003/0118692 A1 | 6/2003 | Wang et al. |
| 2013/0211500 A1 | 8/2013 | Kibbe et al. |
| 2014/0037588 A1* | 2/2014 | Yang ............. A61K 9/0024 424/93.6 |
| 2014/0058049 A1 | 2/2014 | Ameer et al. |
| 2014/0135407 A1 | 5/2014 | Ameer et al. |
| 2014/0155516 A1 | 6/2014 | Ameer et al. |
| 2014/0178504 A1* | 6/2014 | Reynolds ............. A61K 33/00 424/718 |

OTHER PUBLICATIONS

Arshady, Preparation of biodegradable microspheres and microcapsules: 2. Polyactides and related polyesters, vol. 17(1), pp. 1-21, 1991.
Atmaja et al., Targeting of Cancer Cells Using Quantum Dot-Polypeptide Hybrid Assemblies that Function as Molecular Imaging Agents and Carrier Systems,Adv Funct Mater. Dec. 8, 2010;20(23):4091-4097.
Borkow et al., Molecular mechanisms of enhanced wound healing by copper oxide-impregnated dressings, Wound Repair Regen. Mar.-Apr. 2010;18(2):266-75.
Centers for Disease Control and Prevention. National Diabetes Statistics Report: Estimates of Diabetes and its Burden in the United States, 2014. Atlanta, GA: U.S. Department of Health and Human Services:, 2014.
Chen et al., From Bimetallic Metal-Organic Framework to Porous Carbon: High Surface Area and Multicomponent Active Dopants for Excellent Electrocatalysis, Adv Mater. Sep. 9, 2015;27(34):5010-6.
Chen et al., In vivo functional microangiography by visible-light optical coherence tomography,Biomed Opt Express. Sep. 15, 2014;5(10):3603-12.
Cheng et al., Thermosensitive Chitosan-Gelatin-Glycerol Phosphate Hydrogels as a Cell Carrier for Nucleus Pulposus Regeneration: An In Vitro Study, Tissue Eng Part A. Feb. 2010;16(2):695-703.
De Cicco et al., In situ forming antibacterial dextran blend hydrogel for wound dressing: SAA technology vs. spray drying, Carbohydr Polym. Jan. 30, 2014;101:1216-24.
Della Rocca et al., Nanoscale Metal-Organic Frameworks for Biomedical Imaging and Drug Delivery, Acc Chem Res. Oct. 18, 2011;44(10):957-68.
Dioufa et al., Acceleration of wound healing by growth hormone-releasing hormone and its agonists, Proc Natl Acad Sci U S A. Oct. 26, 2010;107(43):18611-5.
Dreifke et al., Current wound healing procedures and potential care, Mater Sci Eng C Mater Biol Appl. Mar. 2015;48:651-62.
Ebrahimian et al., Cell Therapy Based on Adipose Tissue-Derived Stromal Cells Promotes Physiological and Pathological Wound Healing, Arterioscler Thromb Vasc Biol. Apr. 2009;29(4):503-10.
Eming et al., Wound repair and regeneration: Mechanisms, signaling, and translation, Sci Transl Med. Dec. 3, 2014;6(265):2655r6.
Gillespie, Keratin Structure and Changes with Copper Deficiency, Australas J Dermatol. Dec. 1973;14(3):127-31.
Gopal et al., Chitosan-based copper nanocomposite accelerates healing in excision wound model in rats, Eur J Pharmacol. May 15, 2014;731:8-19.
Guo et al., A Comparative Study of Hollow Copper Sulfide Nanoparticles and Hollow Gold Nanospheres on Degradability and Toxicity,ACS Nano. Oct. 22, 2013;7(10):8780-93.
Guo et al., Tuning the Luminescence of Metal-Organic Frameworks for Detection of Energetic Heterocyclic Compounds, J Am Chem Soc. Nov. 5, 2014;136(44):15485-8.
Hanagata et al., Molecular Responses of Human Lung Epithelial Cells to the Toxicity of Copper Oxide Nanoparticles Inferred from Whole Genome Expression Analysis, ACS Nano. Dec. 27, 2011;5(12):9326-38.
He et al., Nanomedicine Applications of Hybrid Nanomaterials Built from Metal-Ligand Coordination Bonds: Nanoscale Metal-Organic Frameworks and Nanoscale Coordination Polymers, Chem Rev. Oct. 14, 2015;115(19):11079-108.
Holland et al., Polymers for biodegradable medical devices. 1. The potential of polyesters as controlled macromolecular release systems, J Controlled Release, vol. 4(3), pp. 155-180, 1986.
Horcajada et al., Porous metal-organic-framework nanoscale carriers as a potential platform for drug delivery and imaging, Nat Mater. Feb. 2010;9(2):172-8.
Hu et al., Luminescent metal-organic frameworks for chemical sensing and explosive detection, Chem Soc Rev. Aug. 21, 2014;43(16):5815-40.
Illum, "Polymers in Controlled Drug Delivery" Wright, Bristol, 1987, TOC only.
Kanno et al., Biofilm formation on rat skin wounds by Pseudomonas aeruginosa carrying the green fluorescent protein gene, Exp Dermatol. Feb. 2010;19(2):154-6.
Liu et al., Hyperoxia, Endothelial Progenitor Cell Mobilization, and Diabetic Wound Healing, Antioxid Redox Signal. Nov. 2008;10(11):1869-82.
Loomba et al., Metallic nanoparticles and their medicinal potential. Part II: aluminosilicates, nanobiomagnets, quantum dots and cochleates,Ther Deliv. Sep. 2013;4(9):1179-96.
Lu et al., Tuning the structure and function of metal-organic frameworks via linker design, Chem Soc Rev. Aug. 21, 2014;43(16):5561-93.
Mandinov et al., Copper chelation represses the vascular response to injury, Proc Natl Acad Sci U S A. May 27, 2003;100(11):6700-5.
Marelli et al., Newly identified interfibrillar collagen crosslinking suppresses cell proliferation and remodelling, Biomaterials. Jun. 2015;54:126-35.
Mason et al., Methane storage in flexible metal-organic frameworks with intrinsic thermal management, Nature. Nov. 19, 2015;527(7578):357-61.
Mudge, Recent accomplishments in wound healing,Int Wound J. Feb. 2015;12(1):4-9.
Nakamura et al., Enhanced wound healing by topical administration of mesenchymal stem cells transfected with stromal cell-derived factor-1, Biomaterials. Dec. 2013;34(37):9393-400.
Nuschke, Activity of mesenchymal stem cells in therapies for chronic skin wound healing, Organogenesis. Jan. 1, 2014;10(1):29-37.
Okawa et al., Proton-Conductive Magnetic Metal-Organic Frameworks, {NR3(CH2COOH)}[MaIIMbIII(ox)3]: Effect of Carboxyl Residue upon Proton Conduction, J Am Chem Soc. Feb. 13, 2013;135(6):2256-62.
Paladini et al., Silver-doped self-assembling di-phenylalanine hydrogels as wound dressing biomaterials, J Mater Sci Mater Med. Oct. 2013;24(10):2461-72.
Pastar et al., Epithelialization in Wound Healing: A Comprehensive Review, Adv Wound Care (New Rochelle). Jul. 1, 2014;3(7):445-464.
Pina et al., Natural-Based Nanocomposites for Bone Tissue Engineering and Regenerative Medicine: A Review, Adv Mater. Feb. 18, 2015;27(7):1143-69.

(56) References Cited

OTHER PUBLICATIONS

Pitt, The controlled parenteral delivery of polypeptides and proteins, Int J Phar, vol. 59(3), pp. 173-196, 1990.

Randeria et al., siRNA-based spherical nucleic acids reverse impaired wound healing in diabetic mice by ganglioside GM3 synthase knockdown, Proc Natl Acad Sci U S A. May 5, 2015;112(18):5573-8.

Sen et al., Copper-induced vascular endothelial growth factor expression and wound healing, Am J Physiol Heart Circ Physiol. May 2002;282(5):H1821-7.

Serrano et al., Novel Biodegradable Shape-Memory Elastomers with Drug-Releasing Capabilities,Adv Mater. May 17, 2011;23(19):2211-5.

Sood et al., Wound Dressings and Comparative Effectiveness Data, Adv Wound Care (New Rochelle). Aug. 1, 2014;3(8):511-529.

Sousa et al., New Frontiers in Cardiology: Drug-Eluting Stents: Part I, Circulation. May 6, 2003;107(17):2274-9.

Sun et al., Dextran hydrogel scaffolds enhance angiogenic responses and promote complete skin regeneration during burn wound healing, Proc Natl Acad Sci U S A. Dec. 27, 2011;108(52):20976-81.

Suresh et al., MOF Nano-Vesicles and Toroids: Self-Assembled Porous Soft-Hybrids for Light Harvesting, Adv Funct Mater, vol. 23(45), pp. 5585-5590, 2013.

Wu et al., Luminescent Metal-Organic Frameworks for Selectively Sensing Nitric Oxide in an Aqueous Solution and in Living Cells, Adv Funct Mater, vol. 22(8), pp. 1698-1703, 2012.

Xiao et al., Exceptional function of nanoporous metal organic framework particles in emulsion stabilisation, Chem Commun (Camb). Sep. 25, 2013;49(74):8208-10.

Yang et al., A Thermoresponsive Biodegradable Polymer with Intrinsic Antioxidant Properties, Biomacromolecules. Nov. 10, 2014;15(11):3942-52.

Yang et al., Synthesis and evaluation of poly(diol citrate) biodegradable elastomers, Biomaterials. Mar. 2006;27(9):1889-98.

Zhang et al., A Facile and General Coating Approach to Moisture/Water-Resistant Metal-Organic Frameworks with Intact Porosity, J Am Chem Soc. Dec. 10, 2014;136(49):16978-81.

Zhang et al., A Family of Metal-Organic Frameworks Exhibiting Size-Selective Catalysis with Encapsulated Noble-Metal Nanoparticles, Adv Mater. Jun. 25, 2014;26(24):4056-60.

Zhao et al., Wound dressings composed of copper-doped borate bioactive glass microfibers stimulate angiogenesis and heal full-thickness skin defects in a rodent model, Biomaterials. 2015;53:379-91.

Zhuang et al., Rapid Room-Temperature Synthesis of Metal-Organic Framework HKUST-1 Crystals in Bulk and as Oriented and Patterned Thin Films, Adv Funct Mater, vol. 21(8), pp. 1442-1447, 2011.

International Search Report of related PCT/US2015/066731, dated Feb. 25, 2016, 11 pages.

* cited by examiner

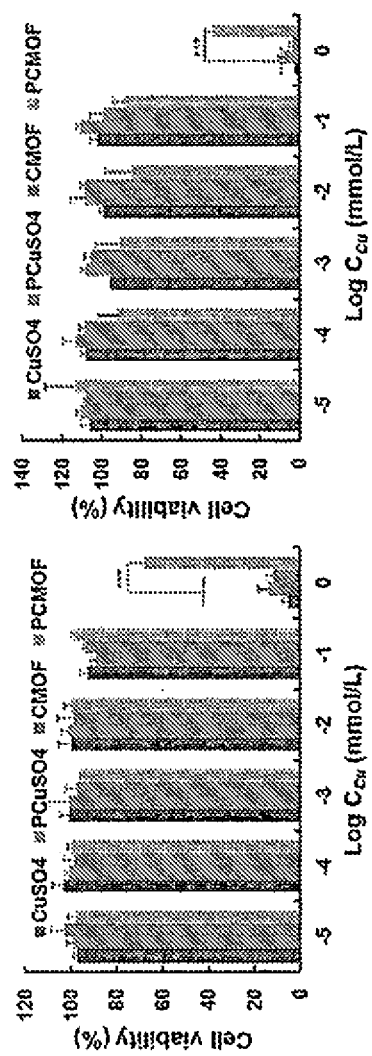

FIG. 4B
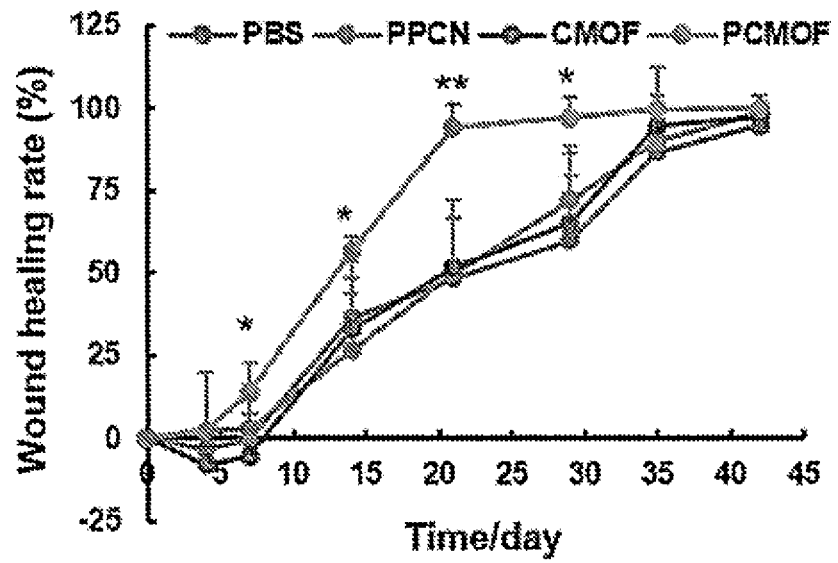
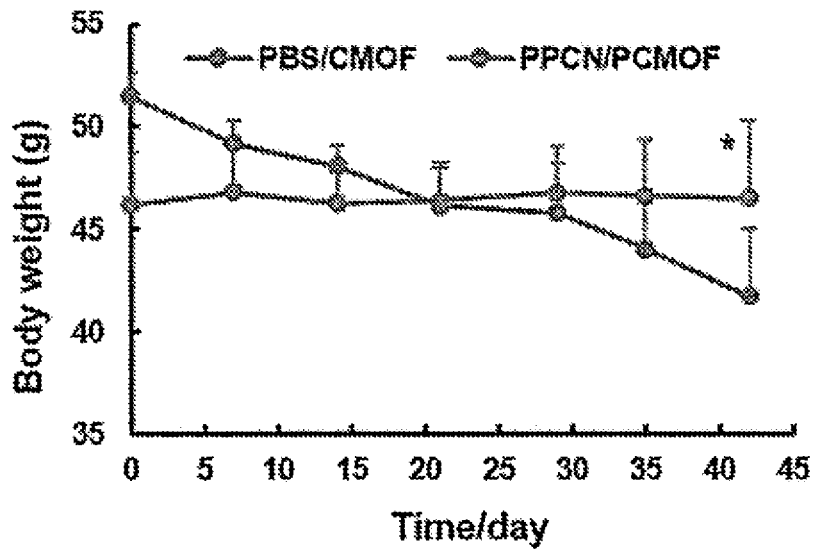
FIG. 4C

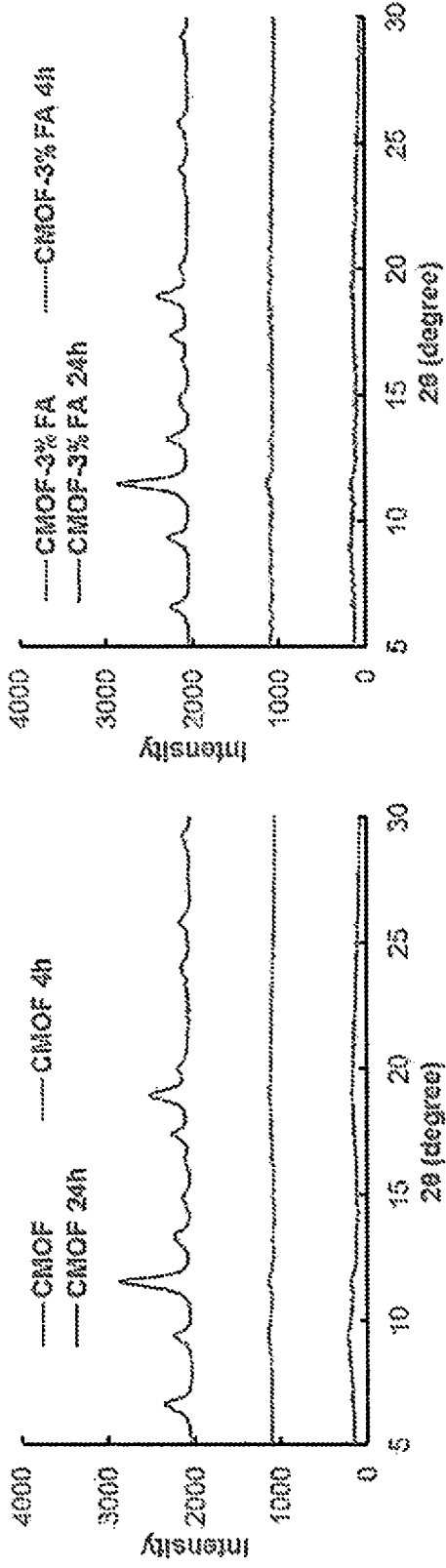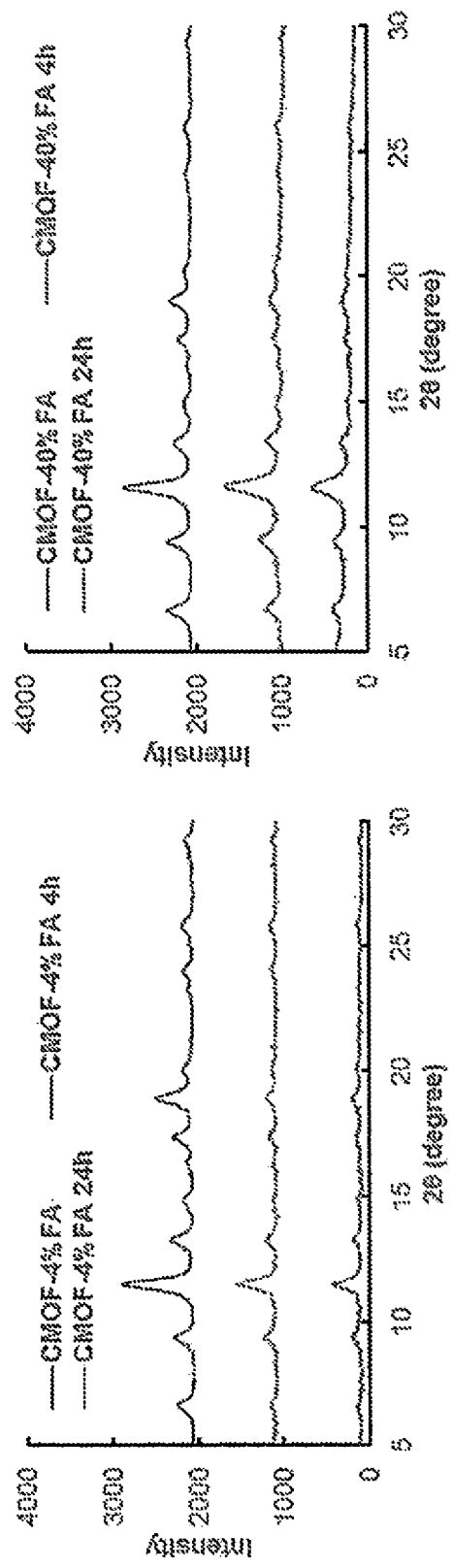
FIG. 7A  FIG. 7B  FIG. 7C  FIG. 7D

POLYMER METAL-ORGANIC FRAMEWORK COMPOSITES

CROSS REFERENCE TO RELATED APPLICATIONS

The present application claims the priority benefit of U.S. Provisional Patent Application 62/094,971, filed Dec. 20, 2014, which is incorporated by reference in its entirety.

STATEMENT REGARDING FEDERAL FUNDING

This invention was made with government support under R01 EB017129 awarded by the National Institutes of Health. The government has certain rights in the invention.

FIELD

Provided herein are polymer and metal organic frameworks (MOFs) composites, and methods of use and preparation thereof. In particular, Poly(polyethyleneglycol citrate-co-N-isopropylacrylamide) (PPCN) and copper MOF composites are provided.

BACKGROUND

Chronic non-healing wounds continue to be a great challenge for physicians and contribute to the increasing healthcare costs (ref 1; herein incorporated by reference in its entirety). In particular, chronic diabetic foot ulcers (DFUs) are responsible for more than 73,000 nontraumatic lower limb amputations and impose substantial burden on public and private payers, ranging from $9-$13 billion in addition to the costs associated with diabetes itself (ref 2; herein incorporated by reference in its entirety). Despite the use of autografts, tissue engineered products, and wound dressings of various types (ref 3; herein incorporated by reference in its entirety), successful treatment of chronic DFUs remains elusive and currently there is no widely used effective therapy (ref 4; herein incorporated by reference in its entirety). Therefore, new cost effective, safe, and efficacious strategies are warranted to improve the care for hard-to-heal DFUs.

Copper is an essential element with a long history of use in humans involved in many wound-healing-related processes (ref 6; herein incorporated by reference in its entirety), including induction of vascular endothelial growth factor (ref 5a: herein incorporated by reference in its entirety), angiogenesis (ref 7; herein incorporated by reference in its entirety), and the expression and stabilization of extracellular skin proteins, such as keratin and collagen (ref 8; herein incorporated by reference in its entirety). Copper sulfate and copper oxide were shown to promote healing in BalbC mice or diabetic mice (refs. 9, 9c; herein incorporated by reference in their entireties), but repeat applications are necessary in some cases once a day, putting the patient at risk of copper toxicity. Elevated non-physiological concentrations of copper ions are toxic because the ion can interfere with the homeostasis of other metals, damage DNA, and generate reactive oxygen species that can adversely modify proteins, lipids and nucleic acids (ref 10; herein incorporated by reference in its entirety).

Metal-organic frameworks (MOFs), also called porous coordination polymers, are a class of crystalline porous materials composed of inorganic metal ions or clusters connected by organic ligands (ref 11; herein incorporated by reference in its entirety). They have been synthesized using a variety of organic ligands including ditopic, tritopic, tetratopic, hexatopic, octatopic, mixed, desymmetrized, metallo, and N-heterocyclic linkers (ref 12; herein incorporated by reference in its entirety). MOFs have typically been used for gas adsorption and separation (ref 13; herein incorporated by reference in its entirety), catalysis (ref 14; herein incorporated by reference in its entirety), luminescence (ref 15; herein incorporated by reference in its entirety), sensing (ref 16; herein incorporated by reference in its entirety), and proton conduction (ref 17; herein incorporated by reference in its entirety). However, MOFs are not stable in physiological protein containing solutions (ref 19; herein incorporated by reference in its entirety), and therefore believed to be unsuitable for use at the wound bed.

SUMMARY

Provided herein are polymer and metal organic frameworks (MOFs) composites, and methods of use and preparation thereof. In particular, Poly(polyethyleneglycol citrate-co-N-isopropylacrylamide) (PPCN) and copper MOF composites are provided.

In some embodiments, provided herein are compositions comprising a composite of: (a) a metal organic framework (MOF); and (b) a polymer. In some embodiments, the MOF comprises MOF nanoparticles. In some embodiments, the nanoparticles are coated in the polymer. In some embodiments, the MOF is encapsulated and/or dispersed within the polymer (e.g., a polymer network). In some embodiments, the polymer network comprises a uncrosslinked polymers, a hydrogel, or a thermoset elastomer. In some embodiments, the MOF comprises transition metal nodes connected by a organic ligands. In some embodiments, the transition metal is selected from the list consisting of: copper (Cu), zinc (Zn), magnesium (Mg), cobalt (co), Nickel, (Ni), iron (Fe), manganese (Mn), palladium (Pd), chromium (Cr), lead (Pb), titanium (Ti), and combinations thereof. In some embodiments, the transition metal is copper. In some embodiments, the organic ligand comprises: (a) a substructure comprising alkyl, cycloalkyl, heteroalkyl, aryl, and heteroaryl groups; the substructure displaying (b) a plurality of metal ion coordination groups. In some embodiments, the metal ion coordination groups comprise COOH groups. In some embodiments, the organic ligand comprises a molecule selected from the list consisting of: 1,4-di(4'-pyrazolyl)benzene, 1,4,7,10-tetraazacyclododecane-n,n',n'',n'''-tetraacetic acid, 2,4,6-(tri-4-pyridinyl)-1,3,5-triazine, tris(isobutylaminoethyl)amine, [1,1'-biphenyl]-4,4'-dicarboxylic acid, 2,5-dihydroxyterephthalic acid, 2,6-naphthalenedicarboxylic acid, 1,4-phenylenediacetic acid, 1,1,2,2-tetra(4-carboxylphenyl)ethylene, 1,3,5-tricarboxybenzene, 1,3,5-tris(4-carboxyphenyl)benzene, and 2-(diphenylphosphino)terephthalic acid. In some embodiments, the MOF comprises copper metal ion nodes linked by 1,3,5-tricarboxybenzene organic ligands. In some embodiments, the polymer comprises a polyester. In some embodiments, the polyester comprises a citric acid polyester. In some embodiments, the citric acid polyester comprises a polydiolcitrate. In some embodiments, the polydiolcitrate comprises poly(polyethyleneglycol citrate-co-N-isopropylacrylamide) (PPCN).

In some embodiments, provided herein are compositions comprising a composite of: (a) copper metal organic framework (CMOF) nanoparticles; and (b) a thermoresponsive polydiolcitrate polymer. In some embodiments, the CMOF nanoparticles are coated in the thermoresponsive polydiolcitrate polymer. In some embodiments, the CMOF nanoparticles are dispersed within the thermoresponsive polydiolcitrate polymer. In some embodiments, the CMOF comprises copper metal ion nodes linked by organic ligands selected from the list consisting of: 1,4-di(4'-pyrazolyl) benzene, 1,4,7,10-tetraazacyclododecane-n,n',n'',n'''-tetraacetic acid, 2,4,6-(tri-4-pyridinyl)-1,3,5-triazine, tris(isobutylaminoethyl)amine, [1,1'-biphenyl]-4,4'-dicarboxylic acid, 2,5-dihydroxyterephthalic acid, 2,6-naphthalenedicarboxylic acid, 1,4-phenylenediacetic acid, 1,1,2,2-tetra(4-carboxylphenyl)ethylene, 1,3,5-tricarboxybenzene, 1,3,5-tris(4-carboxyphenyl)benzene, and 2-(diphenylphosphino)terephthalic acid. In some embodiments, the CMOF comprises copper metal ion nodes linked by 1,3,5-tricarboxybenzene organic ligands. In some embodiments, the polydiolcitrate comprises poly(polyethyleneglycol citrate-co-N-isopropylacrylamide) (PPCN).

In some embodiments, provided herein are compositions comprising a composite of: (a) copper metal organic framework (CMOF) nanoparticles comprising copper metal ion nodes linked by 1,3,5-tricarboxybenzene organic ligand; and (b) poly(polyethyleneglycol citrate-co-N-isopropylacrylamide) (PPCN). In some embodiments, the CMOF nanoparticles are coated in the PPCN. In some embodiments, the CMOF nanoparticles are dispersed within the PPCN.

In some embodiments, provided herein are methods of promoting the healing of a wound comprising administering a polymer/MOF (e.g., polydiolcitrate/CMOF (e.g., PPCN/1,3,5-tricarboxybenzene-CMOF, etc.), etc.) composite described herein to the wound.

In some embodiments, provided herein are wound dressings comprising a wound-contacting surface, wherein the wound contacting surface comprises a polymer/MOF (e.g., polydiolcitrate/CMOF (e.g., PPCN/1,3,5-tricarboxybenzene-CMOF, etc.), etc.) composite described herein. In some embodiments, the wound dressing comprises a dressing selected from the list consisting of: gauze, a bandage, a film dressing, a pad, and a membrane.

In some embodiments, provided herein are methods of treating a wound comprising applying a wound dressing described herein (e.g., having a wound-contacting surface comprising a polymer/MOF (e.g., polydiolcitrate/CMOF (e.g., PPCN/1,3,5-tricarboxybenzene-CMOF, etc.), etc.)) to the wound.

In some embodiments, provided herein is the use of a composition or wound dressing described herein (e.g., comprising or having a wound-contacting surface comprising a polymer/MOF (e.g., polydiolcitrate/CMOF (e.g., PPCN/1,3,5-tricarboxybenzene-CMOF, etc.), etc.)) in the promotion of wound healing.

BRIEF DESCRIPTION OF THE DRAWINGS

FIGS. 2A-E. Cytotoxicity and pro-apoptosis effect of PCMOF. Cytotoxicity of CuSO4, PCuSO$_4$, CMOF and PCMOF on (A) HEKa and (B) HDF cells. (C) Cytotoxicity of PPCN on HEKa and HDF cells. (D and E) Cell apoptosis of (a) HEKa cells and (b) HDF cells after treatment with PPCN, CuSO4, PCuSO$_4$, CMOF, PCMOF at a concentration of 0.5 mmol Cu/L.

FIGS. 4A-C. Effects of PCMOF on chronic wound healing in vivo. A) Photos of wounds in diabetic mice treated with PBS, PPCN, CMOF, and PCMOF. B) Quantitative analysis of wound healing rates. C) Mice body weight changes after PBS, PPCN, CMOF or PCMOF treatment.

FIGS. 7A-D. XRD patterns of CMOF-FA before and after treatment with 10% FBS.

DEFINITIONS

Figure 1A:
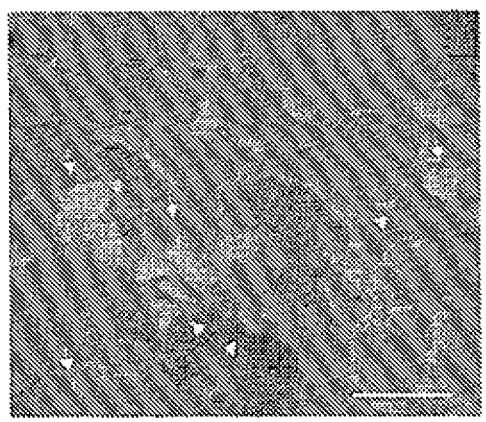
FIGS. 1A-H. Characterization of PCMOF. A) SEM photograph of PCMOF.
White arrows represent CMOF crystals. (Scale bar: 0.5 µm) B) Copper release from PCMOF and PCuSO$_4$ in PBS or 10% FBS. C) Rheological characterizations of PPCN, PCMOF and PCuSO$_4$. The storage modulus G' and loss modulus G'' were plotted logarithmically against temperature (15-40° C. at 10 Hz) of the corresponding hydrogel samples. D) Photos of PPCN, PCuSO$_4$, and PCMOF at room temperature. E) Photos of PPCN, PCuSO$_4$, and PCMOF after treatment with 10% FBS at 37° C. F) ABTS radical scavenging capacity of CuSO$_4$, CMOF, PPCN, PCuSO$_4$ and PCMOF. G) TEM morphology of (a, c) CMOF and (b, d) PCMOF (a, b) before and (c, d) after treatment with 10% FBS at 37° C. (Scale bars: 200 nm). F) XRD patterns of CMOF and PCMOF before and after treatment with 10% FBS.

As used herein, the term "metal-organic framework" ("MOF") refers to compounds comprising metal ions or metal-ion clusters coordinated to organic molecules (e.g., polymers) to form one-, two-, or three-dimensional structures. MOFs typically comprise multiple metal ion or cluster "nodes" linked by organic ligands which form the framework. In typical embodiments, MOFs are stable, crystalline, and/or porous.

As used herein, the term "polymer" refers to a chain of repeating structural units (e.g., citric acid, aliphatic diol, amino acids, etc.) or "monomers", typically of large molecular mass. Examples of polymers include homopolymers (single type of monomer subunits), copolymers (two types of monomer subunits), and heteropolymers (e.g., three or more types of monomer subunits). As used herein, the term "oligomer" refers to a polymer of only a few monomer units (e.g., 2, 3, 4, 5, or more) up to about 50 monomer units, for example a dimer, trimer, tetramer, pentamer, hexamer . . . decamer, etc.

As used herein, the term "linear polymer" refers to a polymer in which the molecules form long chains without branches or crosslinked structures.

As used herein, the term "branched polymer" refers to a polymer comprising a polymer backbone with one or more additional monomers, or chains of monomers, extending from polymer backbone. The degree of interconnectedness of the "branches" is insufficient to render the polymer insoluble.

As used herein, the terms "pre-polymer" and "pre-oligomer" refer to linear or branched polymers and oligomers (e.g., not significantly crosslinked, soluble) that have the capacity to be crosslinked under appropriate conditions, but which have not yet been subjected to the appropriate conditions.

As used herein, the term "crosslinked polymer" refers to a polymer with a significant degree of interconnectedness between multiple polymer strands, the result of which is an insoluble polymer network (e.g., thermoset elastomer). For example, multiple polymer stands may be crosslinked to each other at points within their structures, not limited to the ends of the polymer chains.

As used herein, the term "hydrogel" refers to a three-dimensional (3D) crosslinked network of hydrophilic polymers that swells, rather than being dissolved, in water.

As used herein, the term "thermoresponsive" refers to materials that exhibit altered physical characteristics at different temperature ranges. Particularly relevant herein are "phase-transitioning thermoresponsive materials. Phase-transitioning thermoresponsive" materials are soluble or in a liquid state at a first temperature range (e.g., below 26° C.) and insoluble or in a solid state at a second temperature range (e.g., 30-45° C.). Non-limiting examples of a phase-transitioning thermoresponsive polymers are poly(N-isopropylacrylamide) (PNIPAM) and poly(polyethyleneglycol co-citric acid-co-N isopropylacrylamide).

As used herein, the term "composite" refers to a material comprising two or more molecular, polymeric, and/or supramolecular constituents that are miscible with one another, and may form a single homogeneous material. While covalent connections between the constituent components may be present, they are not required to form or maintain the composite or its homogeneity; rather, non-covalent and/or mechanical/physical interactions and associations are responsible for stabilizing the composite.

As used herein, the term "nanoparticles" refers to particles having mean dimensions (e.g., diameter, width, length, etc.) of less than 1 μm (e.g., <500 nm ("sub-500-nm nanoparticles"), <100 nm ("sub-100-nm nanoparticles"), <50 nm ("sub-50-nm nanoparticles"). Nanoparticles may be of any shape and may be two or three dimensional.

As used herein, the term "biocompatible" refers to materials and agents that are not toxic to cells or organisms. In some embodiments, a substance is considered to be "biocompatible" if its addition to cells in vitro results in less than or equal to approximately 10% cell death, usually less than 5%, more usually less than 1%, and preferably less than 0.1%.

The term "biodegradable," as used to describe the polymers, hydrogels, composites, and/or wound dressings herein, refers to compositions that are degraded or otherwise "broken down" under exposure to physiological conditions. In some embodiments, a biodegradable substance is a broken down by cellular machinery, enzymatic degradation, chemical processes, hydrolysis, etc. In some embodiments, a biodegradeable composition comprises hydrolyzable ester linkages.

As used herein, the phrase "physiological conditions" relates to the range of chemical (e.g., pH, ionic strength) and biochemical (e.g., enzyme concentrations) conditions likely to be encountered in the intracellular and extracellular fluids of tissues. For most tissues, the physiological pH ranges from about 7.0 to 7.4.

As used herein, the term "substantially all," "substantially complete" and similar terms refer to greater than 99%; and the terms "substantially none," "substantially free of," and similar terms refer to less than 1%.

The term "about" allows for a degree of variability in a value or range. As used herein, the term "about" refers to values within 10% of the recited value or range (e.g., about 50 is the equivalent of 45-55).

DETAILED DESCRIPTION

Provided herein are polymer and metal organic frameworks (MOFs) composites, and methods of use and preparation thereof. In particular, Poly(polyethyleneglycol citrate-co-N-isopropylacrylamide) (PPCN) and copper MOF composites are provided.

I. General

In some embodiments, provided herein are cooperative polymer/MOF composites. In some embodiments, the presence of the MOF does not destabilize the polymer, and the polymer protects the MOF from degradation. Metal is reliably and/or consistently released form the composite. In some embodiments, such composites find use in dressings for the treatment of wounds (e.g., chronic wounds); however, they are not so limited. Polymer/MOF composites provide useful materials for the delivery of metal ions for any use.

In some embodiments, provided herein are methods, systems, and compositions to slowly deliver copper ions (e.g., to cells, tissues, subjects, etc.) through the use of copper-based metal organic framework (CMOF) nanoparticles dispersed within a thermoresponsive polydiolcitrate as a synergistic system to fabricate stabilized a CMOF-hydrogel composite for potential use as a wound dressing. In certain embodiments, the present invention is suitable as a novel thermoresponsive dressing to safely accelerate wound healing.

As an exemplary polymer/MOF composite, a composite of Poly(polyethyleneglycol citrate-co-N-isopropylacrylamide)(PPCN) and a copper MOF, referred to herein as "PCMOF" has been prepared successfully and the cooperative effect has been demonstrated between the CMOF and PPCN. CMOF did not destabilize PPCN, and the PPCN protected CMOF the CMOF from degradation (e.g., too rapid of degradation) or rapid copper release. PCMOF sustainably released copper ion, thus showing the capacity to enhance scratch closure with lack of cytotoxicity and significantly accelerating the chronic wound healing in diabetic mice. The functionally cooperating PCMOF provides a useful dressing material for the treatment of, for example, chronic wounds. In addition, PCMOF provides a delivery vehicle for the regulated release of copper at a desired location.

The applications of the compositions, systems, and methods of the present disclosure include, for example: Polydiolcitrate-metal-organic framework nanocomposite can be used to deliver other metal ions (Zr, Al, Zn et al.); Polydiolcitrate-metal-organic framework nanocomposite can be used to address the following health conditions: wound healing, cancer, microbial infection, inflammation and autoimmune disease.

In some embodiments, the synergistically stabilized polymer/MOF composites (e.g., nanocomposites) provide a mechanism to deliver metal ions without destabilizing the thermoresponsive hydrogel. Polymer/MOF (e.g., PCMOF) framework nanocomposite improves wound healing significantly. Polymer/MOF (e.g., PCMOF) nanocomposites are biocompatible, and reduce the toxicity of metal (e.g., copper) ions (e.g., by regulating metal ion release).

In experiments were conducted during development of embodiments herein, poly(polyethyleneglycol citrate-co-N-isopropylacrylamide) (PPCN) was prepared as previously described (J Yang J. Biomacromolecules. 2014 001: 10.1021/bm5010004; herein incorporated by reference). CMOFs were added to a PPCN solution and mixed thoroughly by vortexing to obtain PPCN/CMOF (PCMOF). The PCMOF was treated with 10% FBS and photographed. Rheological measurements were obtained to confirm hydrogel formation. The morphology of CMOF and PCMOF was observed using TEM and SEM. The release of copper from PCMOF was measured in PBS with or without 10% FBS. The cytotoxicity of PCMOF was evaluated by MTT assay, and the effects of PCMOF on wound closure over, time were measured in vitro via a scratch assay on human keratinocytes (HeKa) and human dermal fibroblasts (HDF) cells and in vivo in healthy mice.

II. MOFs

In some embodiments, compositions and composites described herein comprise a metal organic framework component (e.g., the MOF component of a polymer/MOF composite). MOFs comprise two primary components: (i) a metal ion or cluster of metal ions (e.g., nodes), and (ii) an organic ligand (e.g., substructure).

Suitable metals for use in the MOFs herein include, but are not limited to: copper (Cu), zinc (Zn), magnesium (Mg), cobalt (co), Nickel, (Ni), iron (Fe), manganese (Mn), palladium (Pd), chromium (Cr), lead (Pb), titanium (Ti), and combinations thereof. Other metals meeting the physical and chemical requirements for MOF preparation are also within the scope herein. In some embodiments, the metal is a transition metal. In some embodiments, the metals associate with the ligand as metal ions. In other embodiments, metal ion clusters associate with the ligand.

The organic ligand component of a MOF herein comprises a mono-dentate or polydentate compound that, through a coordination group (or multiple coordination groups), binds a metal or a plurality of metals. In some embodiments, an organic ligand component comprises a substructure comprising: an alkyl or cycloalkyl group, comprising 1 to 40 (e.g., 1, 2, 3, 4, 5, 6, 7, 8, 9, 10, 12, 14, 16, 18, 20, 25, 30, 35, 40, or ranges therebetween) carbon atoms; an aryl group comprising 1 to 10 (e.g., 1, 2, 3, 4, 5, 6, 7, 8, 9, 10, or ranges therebetween) phenyl rings; or an alkyl or aryl amine comprising alkyl or cycloalkyl groups having from 1 to 40 (e.g., 1, 2, 3, 4, 5, 6, 7, 8, 9, 10, 12, 14, 16, 18, 20, 25, 30, 35, 40, or ranges therebetween) carbon atoms or aryl groups comprising 1 to 10 10 (e.g., 1, 2, 3, 4, 5, 6, 7, 8, 9, 10, or ranges therebetween) phenyl rings. In some embodiments, a cycloalkyl or aryl substructure comprises 1 to 10 10 (e.g., 1, 2, 3, 4, 5, 6, 7, 8, 9, 10, or ranges therebetween) rings that comprise either of all carbon or a mixture of carbon with nitrogen, oxygen, sulfur, boron, phosphorus, and/or silicon atoms making up the ring(s).

In some embodiments, the organic ligand substructure displays one or more (e.g., 2, 3, 4, 5, 6, 7, 8, 9, 10, 11, 12, 13, 14, 15, 16, or more or ranges there between) coordination groups capable of interacting with metal ions or metal ion clusters. In some embodiments, the linking moiety comprises a substructure having one or more carboxylic acid linking clusters covalently attached. Exemplary coordination groups include: $CO_2H$, $CS_2H$, $NO_2$, $SO_3H$, $Si(OH)_3$, $Ge(OH)_3$, $Sn(OH)_3$, $Si(SH)_4$, $Ge(SH)_4$, $Sn(SH)_4$, $PO_5H$, $AsO_3H$, $AsO_4H$, $P(SH)_3$, $As(SH)_3$, $CH(RSH)_2$, $C(RSH)_3$, $CH(RNH_2)_2$, $C(RNH_2)_3$, $CH(ROH)_2$, $C(ROH)_3$, $CH(RCN)_2$, $C(RCN)_3$, $CH(SH)_2$, $C(SH)_3$, $CH(NH_2)_2$, $C(NH_2)_3$, $CH(OH)_2$, $C(OH)_3$, $CH(CN)_2$, and $C(CN)_3$, wherein R is an alkyl group having from 1 to 10 carbon atoms, or an aryl group comprising 1 to 2 phenyl rings. In some embodiments, organic ligands for use in the MOFs herein comprise coordination groups selected form the molecular classes including, but not limited to: bidentate carboxylics, such as, oxalic acid, malonic acid, succinic acid, glutaric acid, phthalic acid, isophthalic acid, terephthalic acid, etc.; tridentate carboxylics, such as, citric acid, trimesic acid, etc.; azoles, such as, 1,2,3-triazole, pyrrodiazole, etc.; squaric acid; etc.

In some embodiments, the organic ligand comprises a substructure which displays a plurality of coordination groups around its periphery. The substructure may comprise a combination of linear and/or ringed organic groups, as well as hetero atoms and non-coordinating substituents in order to properly position the coordination groups around the substructure. The coordination of multiple metal ions or metal ion clusters by multiple organic ligands creates a framework of metal ion nodes linked by the organic ligands. In some embodiments, a metal ion is coordinated by a single coordination group from each of two or more (e.g., 2, 3, 4, 5, 6, etc.) organic ligands. In some embodiments, a metal ion is coordinated by multiple coordination groups (e.g., 2, 3, 4, 5, 6, etc.) from a single organic ligand. In some embodiments, an organic ligand coordinates 2 or more (e.g., 2, 3, 4, 5, 6, 7, 8, 9 10, 11, 12, 13, 14, 15, 16) metal ions or clusters, thereby linking two or more nodes of the framework.

Exemplary organic ligands include, but are not limited to:

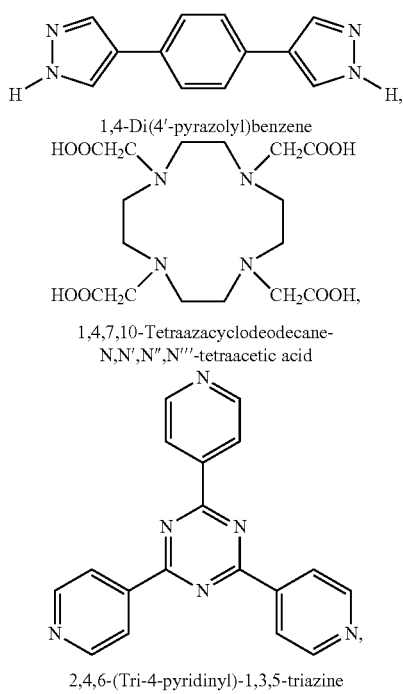

1,4-Di(4'-pyrazolyl)benzene 1,4,7,10-Tetraazacyclodeodecane-N,N',N'',N'''-tetraacetic acid 2,4,6-(Tri-4-pyridinyl)-1,3,5-triazine

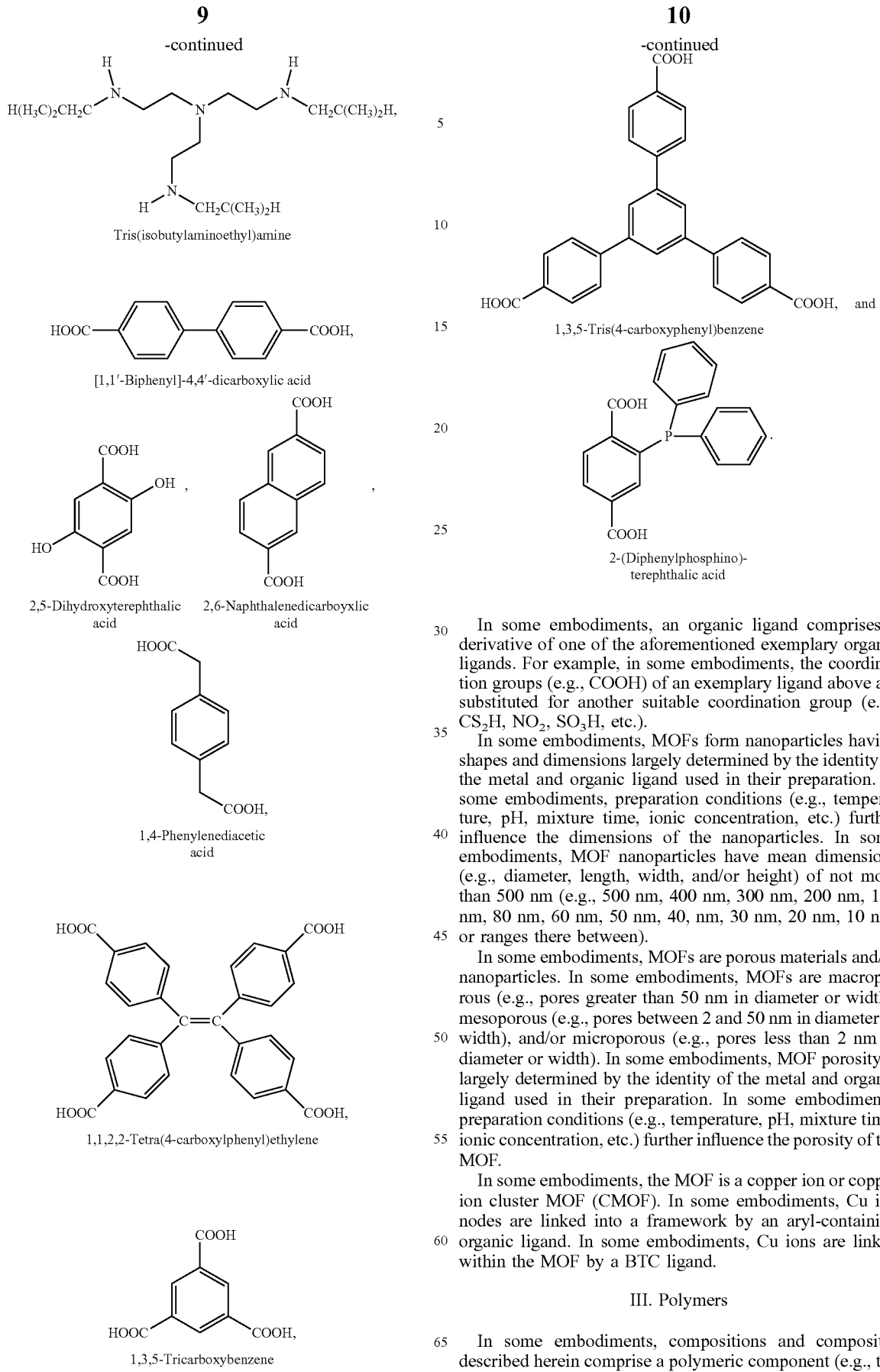

In some embodiments, an organic ligand comprises a derivative of one of the aforementioned exemplary organic ligands. For example, in some embodiments, the coordination groups (e.g., COOH) of an exemplary ligand above are substituted for another suitable coordination group (e.g., $CS_2H$, $NO_2$, $SO_3H$, etc.).

In some embodiments, MOFs form nanoparticles having shapes and dimensions largely determined by the identity of the metal and organic ligand used in their preparation. In some embodiments, preparation conditions (e.g., temperature, pH, mixture time, ionic concentration, etc.) further influence the dimensions of the nanoparticles. In some embodiments, MOF nanoparticles have mean dimensions (e.g., diameter, length, width, and/or height) of not more than 500 nm (e.g., 500 nm, 400 nm, 300 nm, 200 nm, 100 nm, 80 nm, 60 nm, 50 nm, 40, nm, 30 nm, 20 nm, 10 nm, or ranges there between).

In some embodiments, MOFs are porous materials and/or nanoparticles. In some embodiments, MOFs are macroporous (e.g., pores greater than 50 nm in diameter or width), mesoporous (e.g., pores between 2 and 50 nm in diameter or width), and/or microporous (e.g., pores less than 2 nm in diameter or width). In some embodiments, MOF porosity is largely determined by the identity of the metal and organic ligand used in their preparation. In some embodiments, preparation conditions (e.g., temperature, pH, mixture time, ionic concentration, etc.) further influence the porosity of the MOF.

In some embodiments, the MOF is a copper ion or copper ion cluster MOF (CMOF). In some embodiments, Cu ion nodes are linked into a framework by an aryl-containing organic ligand. In some embodiments, Cu ions are linked within the MOF by a BTC ligand.

III. Polymers

In some embodiments, compositions and composites described herein comprise a polymeric component (e.g., the polymer component of a polymer/MOF composite).

Suitable polymers that may find use in embodiments herein (e.g., in the formation of a hydrogel, crosslinked with another polymer, within a composite) include, but are not limited to: collagen, elastin, hyaluronic acid and derivatives, sodium alginate and derivatives, chitosan and derivatives gelatin, starch, cellulose polymers (for example methylcellulose, hydroxypropylcellulose, hydroxypropylmethylcellulose, carboxymethylcellulose, cellulose acetate phthalate, cellulose acetate succinate, hydroxypropylmethylcellulose phthalate), poly(diol citrate) (e.g., poly(octanediol citrate), etc.), casein, dextran and derivatives, polysaccharides, poly (caprolactone), fibrinogen, poly(hydroxyl acids), poly(L-lactide) poly(D,L lactide), poly(D,L-lactide-co-glycolide), poly(L-lactide-co-glycolide), copolymers of lactic acid and glycolic acid, copolymers of ε-caprolactone and lactide, copolymers of glycolide and ε-caprolactone, copolymers of lactide and 1,4-dioxane-2-one, polymers and copolymers that include one or more of the residue units of the monomers D-lactide, L-lactide, D,L-lactide, glycolide, ε-caprolactone, trimethylene carbonate, 1,4-dioxane-2-one or 1,5-dioxepan-2-one, poly(glycolide), poly(hydroxybutyrate), poly(alkylcarbonate) and poly(orthoesters), polyesters, poly (hydroxyvaleric acid), polydioxanone, poly(ethylene terephthalate), poly(malic acid), poly(tartronic acid), polyanhydrides, polyphosphazenes, poly(amino acids), and copolymers of the above polymers as well as blends and combinations of the above polymers. (See generally, Illum, L., Davids, S. S. (eds.) "Polymers in Controlled Drug Delivery" Wright, Bristol, 1987; Arshady, J. Controlled Release 17:1-22, 1991; Pitt, Int. J. Phar. 59:173-196, 1990; Holland et al., J. Controlled Release 4:155-0180, 1986; herein incorporated by reference in their entireties).

In some embodiments, a polymer is selected from a polyester (e.g., poly (polyethyleneglycol citrate) acrylate, poly(polyethyleneglycol co-citric acid-co-N isopropylacrylamide), etc.), poly(diol citrate) (e.g., poly(butanediol citrate), poly(hexanediol citrate), poly(octanediol citrate), poly (decanediol citrate), poly(dodecanediol citrate), poly (hexadecanediol citrate), etc.), poly(hydroxyvalerate), poly (lactide-co-glycolide), poly(hydroxybutyrate), poly (hydroxybutyrate-co-valerate), polyorthoester, polyanhydride, poly(glycolic acid), poly(glycolide), poly(L-lactic acid), poly(L-lactide), poly(D,L-lactic acid), poly(D,L-lactide), poly(caprolactone), poly(trimethylene carbonate), polyester amide, or co-polymers or composites thereof.

In some embodiments, polymeric components comprise citric acid (e.g., a citric acid-based polymer/polyester). Citric acid is a reactive tricarboxylic acid that is part of the Krebs cycle and has been used as a key reactant monomer for the synthesis of polydiolcitrates with a wide range of properties and uses (Yang, J., et al., Synthesis and evaluation of poly(diol citrate) biodegradable elastomers. Biomaterials, 2006. 27(9): p. 1889-98.; U.S. Pat. Nos. 8,772,437; 8,758, 796; 8,580,912; 8,568,765; U.S. Pub. No. 2014/0155516; U.S. Pub. No. 2014/0135407; herein incorporated by reference in their entireties). Depending on the other monomers present in the citric acid polymer, materials are produced with controllable elasticity, biodegradability, thermoresponsiveness, and antioxidant properties (Serrano et al. Adv Mater, 2011. 23(19): p. 2211-5.; Yang J., et al., A thermoresponsive biodegradable polymer with intrinsic antioxidant properties. Biomacromolecules, 2014. 15(11):3942-52.; U.S. Pub. No. 2014/0037588; herein incorporated by reference in its entirety).

In some embodiments, a polymer is the polyesterification product of one or more acids (e.g., succinic acid, glutaric acid, adipic acid, pimelic acid, suberic acid, azelaic acid, sebacic acid, dodecanedioic acid, shorter or longer linear aliphatic diacids, citric acid, isocitric acid, aconitic acid, propane-1,2,3-tricarboxylic acid, trimesic acid, itaconic acid, maleic acid, etc.) and one or more diols or triols (e.g., polyethylene glycol, glycerol, linear aliphatic diol (e.g., butanediol, hexanediol, octanediol, decanediol, dodecanediol, and shorter or longer linear aliphatic diols), etc.). In some embodiments, a polymer is the polyesterification product of an acid (e.g., citric acid), polyethylene glycol, and one or more additional monomeric groups (e.g., glycerol 1,3-diglycerolate diacrylate, N-isoproylacrylamide monomer, etc.).

In some embodiments, any molecular entities capable of reacting with the reactive groups of, for example, citric acid, polyethylene glycol, or the other monomers and polymers described herein, may find use in the generation of polymeric compositions and networks thereof within the scope of the embodiments described herein. For example, additional monomer groups for use in embodiments herein include, but are not limited to: a lactide (e.g., D-lactide, L-lactide, or D,L-lactide), glycolide, lactone, carbonate, thiocarbonate, oxaketocycloalkane, thiooxaketocycloalkane, polyethylene glycol, glycerol, linear aliphatic diol (e.g., butanediol, hexanediol, octanediol, decanediol, dodecanediol, and shorter or longer linear aliphatic diols), linear aliphatic diacid (e.g., succinic acid, glutaric acid, adipic acid, pimelic acid, suberic acid, azelaic acid, sebacic acid, dodecanedioic acid, and shorter or longer linear aliphatic diacids), citric acid, isocitric acid, aconitic acid, propane-1, 2,3-tricarboxylic acid, trimesic acid, diols, triols, polyols, itaconic acid, maleic acid, maleic anhydride, glycerol 1,3-diglycerolate diacrylate, glycerol dimethacrylate, 3-(acryloyloxy)-2-hydroxypropyl methacrylate, N-isopropylacrylamide, etc.

In some embodiments, a composition or composite herein comprises a polymer of citric acid, PEG, and glycerol 1,3-diglycerolate diacrylate (e.g., poly (polyethyleneglycol citrate) acrylate (PPCac), etc.). In some embodiments, a polymer comprises a polymer of citric acid, PEG, glycerol 1,3-diglycerolate diacrylate, and one or more additional monomers (e.g., N-isoproylacrylamide monomer, a diol or triol, etc.). In some embodiments, a polymer is the polymerization product of citric acid, PEG, and glycerol 1,3-diglycerolate diacrylate, and N-isoproylacrylamide monomer (e.g., poly(polyethyleneglycol citrate-co-N-isopropylacrylamide) (PPCN), etc.). In some embodiments, a polymer is the polymerization product of citric acid, PEG, and glycerol 1,3-diglycerolate diacrylate, and N-isoproylacrylamide monomer and one or more additional monomers (e.g., an acid, a diol or triol, etc.). In some embodiments, the polymer is poly(polyethyleneglycol citrate-co-N-isopropylacrylamide) (PPCN). In some embodiments, any of the aforementioned polymers are modified by the inclusion of additional monomers or substituents.

In some embodiments, a polymer comprises one or more linear aliphatic diols (butanediol, hexanediol, octanediol, decanediol, dodecanediol, or any linear aliphatic diol from about 2-20 carbons in length). In certain embodiments, the diol comprises one or more C2-C20 alkyl-diols, C2-C20 alkenyl-diols, or mixtures thereof. In certain other embodiments, the diol comprises one or more C2-C20 alkyl-diols, such as a C6-C20 alkyl-diol, or a C6-C14 alkyl-diol, or a C6-C12 alkyl-diol. For example, the diol can comprise an alkanediol, such as 1,12-dodecanediol, 1,10-decanediol, 1,8-octanediol, or a mixture thereof. In another example, the diol can comprise 1,10-decandediol, 1,8-octanediol, or a mixture thereof. In another example, the diol can comprise 1,8-octanediol (e.g., the polyester is poly(1,8-octanediol-citrate).

Polymers herein may be crosslinked, for example, by optionally including one or more hyperbranching monomers, such as a monomer comprising three alcohol functional groups (a "triol"), in order to control the degradation thereof. For example, glycerol can be added in addition to the citric acid and diol monomer (0-3 mol %, provided the molar ratio of carboxyl and hydroxyl group among the three monomers was maintained as 1/1). Glycerol is a hydrophilic component, and its addition can facilitate the water penetration into the network films which results in the faster degradation rate. Increasing amounts of glycerol can increase the break strength and Young's modulus of the resulting polyester. For example, the Young's modulus can range from 1 to 16 MPa, with strengths and strains at break of up to 10 MPa and 500%, respectively. Depending on the synthesis conditions, total degradation time may range from months to years.

In some embodiments, a polymer comprises additional substituents or functional groups appended to the polymer.

In some embodiments, reagents, monomer components of polymers, methods, reaction conditions, etc. that find use in embodiments described herein are described in: U.S. Pat. Nos. 8,911,720; 8,772,437; 8,758,796; 8,580,912; 8,568,765; 8,404,264; U.S. Pub. No. 2014/0058049; U.S. Pub. No. 2013/0211500; U.S. Prov. App. No. 62/160,334; herein incorporated by reference in their entireties.

In some embodiments, the polymeric component is a pre-polymer, linear polymer, branched polymer, crosslinked polymer, hydrogel, elastomer, etc.

In some embodiments, materials comprise a poly(glycerol-diacid). A poly(glycerol-diacid), as used herein, is a polyester which is prepared from a triol monomer, glycerol, and a second monomer comprising two carboxylic acid functional groups (a "diacid") according to methods familiar to one skilled in the art. For example, suitable poly(glycerol-diacid)s can be prepared as described in U.S. Patent Application Publication No. 2003/0118692, which is hereby incorporated by reference in its entirety. Examples of diacids include, but are not limited to, aromatic-diacids (e.g., terephthalic acid and carboxyphenoxypropane), C2-C20 alkyl-diacids, C2-C20 alkenyl-diacids, and mixtures thereof. The diacids may also include substituents as well. Reactive groups like amine and hydroxyl will increase the number of sites available for cross-linking Amino acids and other biomolecules will modify the biological properties of the polymer. Aromatic groups, aliphatic groups, and halogen atoms will modify the inter-chain interactions within the polymer.

In some embodiments, materials and composites comprise polymers of citric acid, polyethylene glycol, and glycerol 1,3-diglycerolate diacrylate. In some embodiments, citric acid, polyethylene glycol, and glycerol 1,3-diglycerolate diacrylate are polymerized to form a polymer (e.g., pre-polymer) of poly(polyethyleneglycol citrate) acrylate (PPCac). In some embodiments, materials and composites comprise polymers of citric acid, polyethylene glycol, glycerol 1,3-diglycerolate diacrylate, and N-isopropylacrylamide (NIPAAm). In some embodiments, PPCac and NIPAAm are reacted together to produce a poly(polyethyleneglycol citrate co N-isopropylacrylamide (PPCN) polymer. In some embodiments, PPCN is provided as a material.

In some embodiments, polymers herein (e.g., PPCN or another polymer) comprise at least 0.1% citric acid monomers (e.g., >0.1%, >0.2%, >0.5%, >1%, >2%, >3%, >4%, >5%, >10%, >20%, >30%, >40%, >50%, >60%, >70%, >80%, >90%, >95%, >98%, >99%). In some embodiments, polymers herein comprise less than 99% citric acid monomers (e.g., <99%, <98%, <95%, <90%, <80%, <70%, <60%, <50%, <40%, <30%, <20%, <10%, <5%, <4%, <3%, <2%, <1%, <0.5%). In some embodiments, polymers comprise about 99%, about 98%, about 95%, about 90%, about 80%, about 70%, about 60%, about 50%, about 40%, about 30%, about 20%, about 10%, about 5%, about 4%, about 3%, about 2%, about 1%, or about 0.5% citric acid monomers.

In some embodiments, polymers herein (e.g., PPCN or another polymer) comprise at least 0.1% polyethylene glycol monomers (e.g., >0.1%, >0.2%, >0.5%, >1%, >2%, >3%, >4%, >5%, >10%, >20%, >30%, >40%, >50%, >60%, >70%, >80%, >90%, >95%, >98%, >99%). In some embodiments, polymers herein comprise less than 99% polyethylene glycol monomers (e.g., <99%, <98%, <95%, <90%, <80%, <70%, <60%, <50%, <40%, <30%, <20%, <10%, <5%, <4%, <3%, <2%, <1%, <0.5%). In some embodiments, polymers comprise about 99%, about 98%, about 95%, about 90%, about 80%, about 70%, about 60%, about 50%, about 40%, about 30%, about 20%, about 10%, about 5%, about 4%, about 3%, about 2%, about 1%, or about 0.5% polyethylene glycol monomers.

In some embodiments, polymers herein (e.g., PPCN or another polymer) comprise at least 0.1% glycerol 1,3-diglycerolate diacrylate monomers (e.g., >0.1%, >0.2%, >0.5%, >1%, >2%, >3%, >4%, >5%, >10%, >20%, >30%, >40%, >50%, >60%, >70%, >80%, >90%, >95%, >98%, >99%). In some embodiments, polymers herein comprise less than 99% glycerol 1,3-diglycerolate diacrylate monomers (e.g., <99%, <98%, <95%, <90%, <80%, <70%, <60%, <50%, <40%, <30%, <20%, <10%, <5%, <4%, <3%, <2%, <1%, <0.5%). In some embodiments, polymers comprise about 99%, about 98%, about 95%, about 90%, about 80%, about 70%, about 60%, about 50%, about 40%, about 30%, about 20%, about 10%, about 5%, about 4%, about 3%, about 2%, about 1%, or about 0.5% glycerol 1,3-diglycerolate diacrylate monomers.

In some embodiments, polymers and materials herein (e.g., PPCN or another polymer) comprise at least 0.1% N-isopropylacrylamide monomers (e.g., >0.1%, >0.2%, >0.5%, >1%, >2%, >3%, >4%, >5%, >10%, >20%, >30%, >40%, >50%, >60%, >70%, >80%, >90%, >95%, >98%, >99%). In some embodiments, polymers herein comprise less than 99% N-isopropylacrylamide monomers (e.g., <99%, <98%, <95%, <90%, <80%, <70%, <60%, <50%, <40%, <30%, <20%, <10%, <5%, <4%, <3%, <2%, <1%, <0.5%). In some embodiments, polymers comprise about 99%, about 98%, about 95%, about 90%, about 80%, about 70%, about 60%, about 50%, about 40%, about 30%, about 20%, about 10%, about 5%, about 4%, about 3%, about 2%, about 1%, or about 0.5% N-isopropylacrylamide monomers.

In some embodiments, provided herein are composites of the polymers, hydrogels, materials described herein (e.g., poly(polyethyleneglycol citrate co N-isopropylacrylamide (PPCN)) with additional components (e.g., MOF). For example, materials may be used with one or more biodegradable polymers to form a composite material.

In some embodiments, a PPCN composite material comprises at least 0.1% PPCN (e.g., >0.1%, >0.2%, >0.5%, >1%, >2%, >3%, >4%, >5%, >10%, >20%, >30%, >40%, >50%, >60%, >70%, >80%, >90%, >95%, >98%, >99%). In some embodiments, a PPCN composite material comprises less than 99% PPCN (e.g., <99%, <98%, <95%, <90%, <80%, <70%, <60%, <50%, <40%, <30%, <20%, <10%, <5%, <4%, <3%, <2%, <1%, <0.5%). In some embodiments, a PPCN composite material comprises PPCN in an amount of about 99%, about 98%, about 95%, about 90%, about 80%, about 70%, about 60%, about 50%, about 40%, about 30%, about 20%, about 10%, about 5%, about 4%, about 3%, about 2%, about 1%, about 0.5%, or ranges therein. The aforementioned percentages may be wt % or molar %.

Composites may also be made of PPCN (or other polymeric materials) and a non-biogregradable polymer, such as: silicone rubber, polyethylene, acrylic resins, polyurethane, polypropylene, and polymethylmethacrylate (e.g., which is further combined in a composite with a MOF). Composites of PPCN and non-polymeric materials are also within the scope of embodiments described herein. Such non-polymer components include, but are not limited to a bioceramic (e.g., hydroxyapatite, tricalcium phosphate, etc.), nanoparticles (e.g., MOF, iron oxide, zinc oxide, gold, etc.), cosmetic ingredients (e.g., glycerin, glyceryl dilaurate, diisobutyl adipate, mineral oil, dimethicone, pentylene glycol, cyclopentasiloxane, etc.) and tattoo inks (e.g. glycerin, propylene glycol, etc.).

In some embodiments, synthesis of the polymers, hydrogels, networks, etc. described herein are produced by combination of the component molecules (e.g., citric acid, polyethylene glycol and glycerol 1,3-diglycerolate diacrylate; PPCac and NIPAAm, etc.) under the appropriate conditions (e.g., temperature, pressure, pH, etc.). In some embodiments, reaction, crosslinking, polymerization, etc. occurs upon combination of the components under appropriate conditions in the absence of any additional enzyme or chemical catalysts. In some embodiments, a radical initiator (e.g., AIBN) is used to induce a reaction or polymerization.

In some embodiments, components (e.g., citric acid, polyethylene glycol and glycerol 1,3-diglycerolate diacrylate; etc.) are heated to at least 100° C. (e.g., 100° C., 110° C., 120° C., 130° C., 140° C., 150° C., 160° C., 170° C., 180° C., 190° C., 200° C., or more). In some embodiments, components (e.g., PPCac and NIPAAm, etc.) are heated to at least 40° C. (e.g., 40° C., 50° C., 60° C., 70° C., 80° C., 90° C., 100° C., 110° C., 120° C., or more). In some embodiments, components are reacted at a temperature not exceeding 250° C. (e.g., <240° C., <220° C., <200° C., <180° C., <160° C., or less).

In some embodiments, components (e.g., citric acid, polyethylene glycol and glycerol 1,3-diglycerolate diacrylate; PPCac and NIPAAm, etc.) are reacted for at least 1 minute (e.g., >1 minute, >2 minutes, >3 minutes, >4 minutes, >5 minutes, >10 minutes, >20 minutes, >30 minutes, >45 minutes, >1 hour, >2 hours, >3 hours, >4 hours, >12 hours, >24 hours, >48 hours, >72 hours, or more).

In some embodiments, citric acid, polyethylene glycol and glycerol 1,3-diglycerolate diacrylate are reacted at a ratio of 5:9:1, 5:8:2, 5:7:3, 5:6,4, 5:5:5, 4:9:2, 3:9:3, 2:9:4, 1:9:5, 6:8:1, 7:7:1, 8:6:1, 9:5:1, 10:4:1, 11:3:1, 12:2:1, 13:1:1, 4:10:1, 3:11:1, 2:12:1, 1:13:1, or any other suitable ratios thereof or ranges there between. In some embodiments, PPCac and NIPAAm are reacted at a ratio of 10:1, 9:1, 8:1, 7:1, 6:1, 5:1, 4:1, 3:1, 2:1, 1:1, 1:2, 1:3, 1:4:1:5, 1:6, 1:7, 1:8, 1:9, 1:10, or any other suitable ratios thereof or ranges there between.

IV. Composites

Provided herein are composites of a polymeric component and a MOF component. In some embodiments, the composite is prepared by adding the MOF to a solution of the polymeric component (e.g., in aqueous solution, in buffer, etc.). In some embodiments, dissolved MOF is added to a solution of the polymeric component. In some embodiments, MOF is added to a liquid preparation of the polymeric component (e.g., above the melt temperature). In some embodiments, dissolved MOF is added to a liquid preparation of the polymeric component. In any of the above mentioned combinations, the polymeric component may be added to the MOF, or vice versa.

In some embodiments, a composite is formed from a MOF and a pre-polymer of the polymeric component and the polymeric component is crosslinked upon or following composited formation. In some embodiments, a composite is formed by combining a MOF and the monomeric constituents of a polymer; following combination of the components of the MOF, conditions are applied that result in polymerization of the monomers (e.g., around the MOF). In some embodiments, a composite is formed from a MOF and a polymer (e.g., linear, branched, crosslinked, etc.) without additional manipulation (e.g., crosslinking, polymerization, etc.) of the polymer.

In some embodiments, composites are prepared to have a final metal ion concentration of between 0.001 mol/L and 10 mol/L (e.g., 0.001 mol/L, 0.002 mol/L, 0.005 mol/L, 0.1 mol/L, 0.2 mol/L, 0.5 mol/L, 1 mol/L, 2 mol/L, 5 mol/L, 1 mol/L, and ranges there between).

In some embodiments, composite formation is carried out at a temperature between 15° C. and 200° C. (e.g., 15° C., 20° C., 25° C., 30° C., 35° C., 40° C., 45° C., 50° C., 55° C., 60° C., 65° C., 70° C., 75° C., 80° C., 85° C., 90° C., 95° C., 100° C., 110° C., 120° C., 130° C., 140° C., 150° C., 160° C., 170° C., 180° C., 190° C., 200° C., or any ranges there between).

In some embodiments, composites comprise polymer-coated MOFs (e.g., polymer-coated MOF nanoparticles).

In other embodiments, composited comprise MOFs (e.g., MOF nanoparticles) embedded within a polymer, hydrogel, elastomer, etc.

In some embodiments, composites retain all or a portion (e.g., >50%, >60%, >70%, >80%, >90%, >95%, >99%) or even exceed (e.g., 1.5-fold, 2-fold, 3-fold, 4-fold, 5-fold, 6-fold, 7-fold, 8-fold, 9-fold, 10-fold, or more, or ranges therebetween) of one or more characteristics of the MOF and/or polymer components of the composite. Such characteristics may include, thermoresponsiveness, metal-release rate, antioxidance, biodegradation rate, biocompatibility, flexibility, strength, porosity, etc.

V. Applications

The composites and other compositions described herein find use in a variety of fields, and may be used in any suitable applications in which the polymers and/or MOFs described herein find use. In some embodiments, composites find use in any application in which the controlled release and/or exchange of metal ion is desired, particularly from a biocompatible material. Of particular interest is the use of the composites described herein in wound healing and tissue regeneration and repair applications.

In some embodiments, polymer/MOF composites are configured for application directly to a wound or other in vivo site (e.g., damaged tissue, diseased site, surgical site, etc.). In some embodiments, the thermoresponsive and/or adhesive properties of a polymer/MOF composite material allow for the material to stay in place upon application to the wound. In some embodiments, thermoresponsive properties of the polymer/MOF allow for application of the carrier to the wound as a liquid (e.g., at room temperature) followed by gelling of the material upon temperature increase to physiologic conditions. In some embodiments, the polymer/MOF is shaped to fit on or within a wound. The polymer/MOF may be applied in the form of an amorphous gel, a wafer, a thin sheet, etc. In some embodiments, an adhesive is applied to the polymer/MOF (e.g., the boarders of the material) to assist in securing the carrier to the wound.

In some embodiments, the polymer/MOF comprises or is applied to the wound-contacting face of a wound dressing. Suitable wound dressings include gauze, a bandage, a film dressing, a p ad, membrane, etc. Suitable dressings that may be used in conjunction with embodiments erein (e.g., modified to have a wound-contacting face comprising a polymer/MOF described herein) include, for example, those described in: U.S. Pat. No. 4,732,146 to Fasline et al., U.S. Pat. No. 4,917,112 to Kalt, U.S. Pat. No. 4,909,243 to Frank et al., U.S. Pat. No. 4,907,579 to Kum, U.S. Pat. No. 5,167,613 to Karami et al., U.S. Pat. No. 3,779,242 to McCullough, U.S. Pat. No. 4,709,695 to Kohn et al., U.S. Pat. No. 4,399,816 to Spangler, U.S. Pat. No. 5,086,763 to Hathman, and U.S. Pat. No. 4,926,883 to Strock, all of which is herein incorporated by reference in their entireties.

In some embodiments, the composites described herein are configured to deliver additional agents (e.g., therapeutic agents, etc.). In some embodiments, agents are embedded within a polymer/MOF composite during formation of the composite.

In other embodiments, an agent is embedded within a polymer/MOF composite post-preparation (e.g., by soaking). In some embodiments, a polymer/MOF material is coated in an agent. In some embodiments, an additional agent is one that provides additional functionality to the composite (e.g., wound healing, tissue repair, antibacterial, antiseptic, analgesic, etc.).

In some embodiments, polymer/MOF composites are configured for delivery to a subject. In some embodiments, they are administered at the surface of a wound. In other embodiments, they may be applied subdermally or otherwise injected beneath a wound.

EXPERIMENTAL

Example 1

Materials and Methods

Materials, Cell Lines and Animals

Copper acetate monohydrate and $H_3BTC$ were purchased from Alfa Aesar (Ward Hill, Mass.). Citric acid, poly(ethylene glycol) (PEG), glycerol 1,3-diglycerolate diacrylate, 2,2-Azobisisobutyronitrile (AIBN), NIPAM, and MTT were obtained from Sigma-Aldrich (St. Louis, Mo.).

HEKa cells were purchased from Lonza and cultured with keratinocyte growth media (KGM) (Lonza, Walkersville, Md.). HDF cells were obtained from Life technologies (Grand Island, N.Y.) and cultured in Dulbecco's Modified Eagle's Medium (DMEM) containing 10% FBS, 100 Unit/mL penicillin G sodium, and 100 µg/mL streptomycin sulfate. Cells were maintained at 37° C. in a humidified and 5% $CO_2$ incubator.

Diabetic (db/db) mutant mice (BKS.Cg-m$^{+/+}$ Leprdb, #000642; Homozygous for Lepr$^{db}$) were obtained from Jackson Laboratory (Bar Harbor, Me.). Protocols were approved by Institutional Animal Care and Use Committee (IACUC) of Northwestern University.

Preparation and Characterization of PCMOF

CMOF was synthesized according to previously reported method (ref 30; incorporated herein by reference in its entirety). Copper acetate monohydrate (0.15 g, 0.75 mmol) dissolved in distilled water (2 mL) was dropwise added to $H_3BTC$ (0.11 g, 0.5 mmol) dissolved in ethanol (2 mL), followed by stirring at room temperature for 20 min to form gel-like dark turquoise suspension. The suspension was then centrifuged and the precipitate was washed with ethanol/water (1:1 v/v) solution twice to obtain purified CMOF.

PPCN was synthesized as reported previously (ref 21; herein incorporated by reference in its entirety). Firstly, poly (polyethyleneglycol citrate) acrylate prepolymer (PPCac) was prepared with citric acid, PEG and glycerol 1,3-diglycerolate diacrylate through polycondensation reaction. AIBN was added as free radical initiator and PPCac was reacted with pre-purified N-isopropylacrylamide monomers (NIPAM) overnight through free radical polymerization process. Thereafter, PPCN was obtained by precipitation and purification with diethyl ether. The obtained PPCN was then dissolved in PBS, neutralized to pH 7.4 with sodium hydroxide and stored as lyophilized powder for further use.

PCMOF was prepared by adding CMOF to PPCN solution (100 mg/mL) to a copper concentration of 0.1 mol/L under vortexing at room temperature. As controls, $CuSO_4$-loaded PPCN hydrogels ($PCuSO_4$) were also prepared using the same procedure. The morphology of PCMOF was visualized using quick-freeze deep etch (QFDE) method (ref 21; incorporated herein by reference in its entirety). PCMOF solution was placed directly on the QFDE specimen disks, heated at 45° C. until solid, and slam frozen. After etching, an exact replica of exposed gel structure was made, coated with Pt (Thickness: 3.9 nm) and Carbon (Thickness: 3.1 nm), and examined using SEM.

The release of copper from PCMOF or $PCuSO_4$ in 0.1 M PBS (pH 7.4, 37° C.) or 10% FBS (pH 7.4, 37° C.) were assessed. PCMOF solution (80 µL) was added into tubes, allowed to solidify at 37° C. for 5 min and gently rinsed with 0.1 M PBS (pH 7.4, 37° C.). Samples were incubated in 5 mL PBS or 10% FBS and continuously shaken with a speed of 100 rpm at 37° C. At predetermined intervals, 1 mL of release media was taken out for content measurement and replenished with an equal volume of fresh media at 37° C. The amount of the released copper ion was measured by inductively coupled plasma mass spectrometry (ICP-MS).

The stability of PPCN after the load of CMOF was investigated through observing the morphology changes upon the addition of CMOF at room temperature and after treatment with 10% FBS at 37° C., respectively. The rheology of PCMOF was determined by discovery hybrid rheometers (TA Instruments). The storage (elastic) modulus G' and loss (viscous) modulus G" versus temperature were measured between 15 and 40° C. using a constant heating rate of 2° C./min. The temperature at the cross point of G' and G" was defined as gelation temperature.

The ability of PCMOF to scavenge the free radical cation, 2,2'-azino-bis(3-ethylbenzthiazoline-6-sulfonic acid) (ABTS) was assessed. The ability of PPCN gels to scavenge the free radical cation, 2,2'-azino-bis(3-ethylbenzthiazoline-6-sulfonic acid) (ABTS) was assessed. A stock solution of 7 mM ABTS and 2.45 mM sodium persulfate in MQ water was prepared and left overnight in the dark at room temperature, after which the solution was sequentially filtered with 0.45 μm filter. This working solution was then exposed to samples (PBS, CuSO$_4$, CMOF, PPCN, PCuSO$_4$, PCMOF; Cu: 5×10$^{-4}$ μmol/mL; PPCN: 50 mg/mL) and incubated at 37° C. At each time point, ABTS solution was sampled, diluted with MQ water 1:8 and the absorbance measured at 734 nm. All measurements were performed in triplicate. The antiradical activity was measured as % inhibition of free radicals by measuring the decrease in absorbance compared to PBS solutions at different time points.

Stability of CMOF in PCMOF Against FBS Degradation

PCMOF gel was treated with 10% FBS at 37° C. for 1 h, centrifuged at 4° C. for 5 min at the speed of 10,000 rpm, washed twice with ice cold water and resuspended with 50% ethanol. Thereafter, the morphology of PCMOF was observed with transmission electron microscopy (TEM). CMOF with the same treatment was used as control.

After treatment with 10% FBS at 37° C. for 1 h and 4 h, PCMOF gel were frozen with liquid nitrogen and dried with freeze dryer overnight. The crystalline form of PCMOF was determined by X-ray diffraction. CMOF with the same treatment was used as control.

Cytotoxicity Assay

HEKa and HDF cells seeded in 96-well plates (5×10$^3$ cells/well) were incubated with a series of concentrations of PPCN, CuSO$_4$, PCuSO$_4$, CMOF or PCMOF for 48 h. Then, MTT solution was added to each well to a concentration of 0.5 mg/mL and incubated for an additional 4 h. After that, the medium was removed and 100 μL of dimethyl sulfoxide was added to dissolve crystals formed by living cells. Absorbance at 570 nm was measured using a microplate reader. Cell viability was expressed as a percentage of the absorbance to that of the control experiment without treatment.

Apoptosis Assay

HEKa and HDF cells seeded in 12-well plates (4×10$^4$ cells/well) were incubated with PPCN, CuSO$_4$, PCuSO$_4$, CMOF or PCMOF (Cu: 0.5 mmol/L) for 24 h. Cells were harvested, washed twice with ice-cold PBS, stained with Alexa Fluor 488 conjugated Annexin V and PI for 15 min at room temperature in dark, and then analyzed by flow cytometry.

Scratch Assay

HEKa and HDF cells were seeded in 24-well plates (2×10$^4$ cells/well) and allowed to form a confluent monolayer. After starvation with FBS-free medium for 24 h, the cell monolayer was scratched in a straightline using 200 μL pipette tip to mimic an incisional wound. Cells were then washed with PBS to remove cell debris and treated with PPCN, CuSO$_4$, PCuSO$_4$, CMOF or PCMOF (Cu: 1×10$^{-3}$ mmol/L) and incubated at 37° C. with the medium containing 1% FBS. At desired time intervals, cells were photographed and cell migration rate was calculated using the formula shown as below:

$$\% \text{ wound cloure} = \frac{A0 - At}{A0} \times 100$$

$A0$: The scratch area at 0 h;

$At$: The scratch area without cell migration at different time points

Wound Healing In Vivo

The mice (8-10 weeks of age) were anesthetized with isoflurane and the hair on the back of the mice was shaved and completely removed with depilatory cream. After disinfection with betadine and alcohol swabs, mice were subcutaneously injected with buprenorphine (0.5 mg/kg) and two wounds were gently outlined by a marked 6 mm punch biopsy (Acuderm, Fort Lauderdale, Fla.) on each side of the mouse. Following the outline, full-thickness wounds were made using a McPherson-Vannas Micro Scissor (World Precision Instruments, Sarasota, Fla.) and fixed with sterilized and donut-shaped splints. After that, the mice were randomly divided into two groups (n=6). Animals where one wound was treated with PBS (40 μL) and the other with CMOF (Cu: 1 mmol/L, 40 μL) and animals where one wound was treated with PPCN (100 mg/mL, 40 μL) and the other with PCMOF (Cu: 1 mmol/L, 40 μL). After that, wounds were covered with Tegaderm and coban, animals were individually caged, and formulations were reapplied twice a week in the first two weeks and once a week after two weeks. In addition, the mice were weighed once a week during the experiment.

The in vivo non-invasive label-free assessment of angiogenesis at the wound site was performed by quantifying the microvascular sO$_2$ level using functional microangiography by visible light OCT (ref 31; herein incorporated by reference in its entirety). Also, the wounds were photographed with digital camera, wound pixel area was calculated with Image J and normalized to the fixed inner area of the splint. The wound closure rate was calculated with a formula as below:

$$\% \text{ wound closure} = \left(1 - \frac{\left(\frac{\text{wound area}}{\text{splint area}}\right) \text{Day } x}{\left(\frac{\text{wound area}}{\text{splint area}}\right) \text{Day } 0}\right) \times 100$$

Histopathological Analysis

The whole wound tissues with a margin of around 2 mm of ambient unwounded skin was excised at the end time point, fixed with 4% paraformaldehyde for 24 h, embedded in paraffin, and sectioned into 7 μm thickness slices for hematoxylin/eosin (H&E) and Masson's trichrome staining. The development of neovascularization, epidermis, granulation tissues and collagen deposition were inspected.

Example 2

Results

Figure 1B:
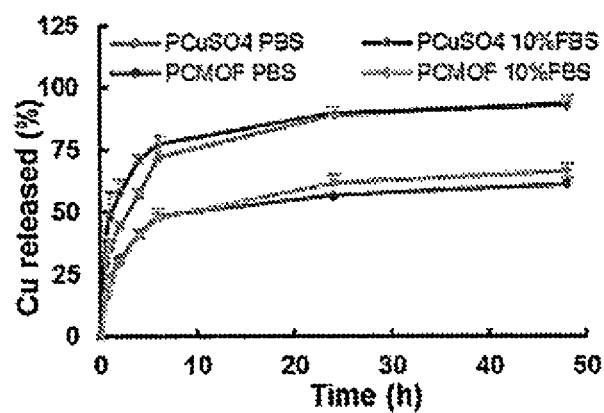

PPCN-CMOF Interactions Enable Sustained Copper Ion Release and Maintenance of Thermoresponsive Gelation Behavior CMOFs were successfully obtained following the reaction between copper acetate monohydrate and 1,3,5-benzenetricarboxylic acid ($H_3BTC$). PPCN was also successfully synthesized. CMOF nanoparticles were added to a PPCN solution of 100 mg/ml resulting in a homogenous dispersion (PCMOF). Scanning electron microscopy (SEM) imaging, confirmed the presence of CMOF crystals within the hydrogel (FIG. 1A). Given the literature describing the use of $CuSO_4$ in wound healing applications, $CuSO_4$ was added to PPCN to create a copper ion-containing hydrogel ($PCuSO_4$). The addition of copper to PPCN in the form of CMOF resulted in the sustained release of copper ions in phosphate buffered saline (PBS) for approximately 24 hrs without any significant change in the PPCN gelation properties. $PCuSO_4$ released 88.7% or 89.5% cumulative release of copper ion whereas PCMOF released 56.5% or 61.5% of copper ions in 24 h in PBS or 10% FBS, respectively (FIG. 1B). The lower copper release amount for PCMOF may be due to the synergetic effect between CMOF and PPCN that stabilize CMOF.

Figure 1C:
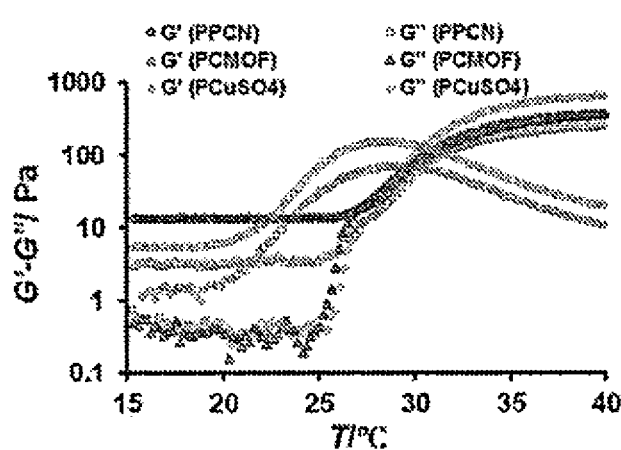
Figure 1D:
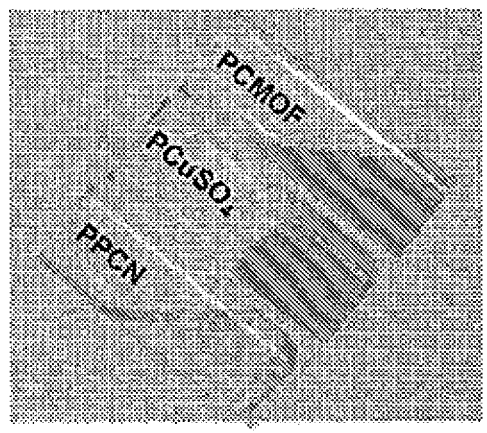
Figure 1E:
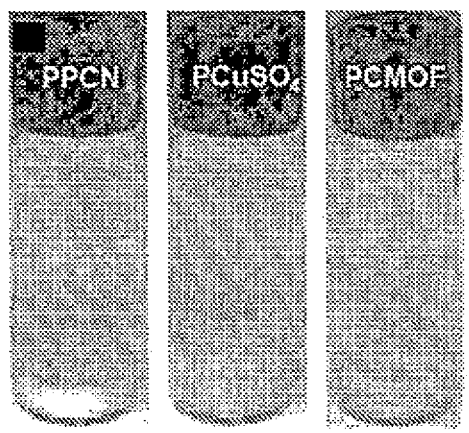

The LCSTs of PPCN and PCMOF were determined via rheology to be 28.4° C. and 26.1° C., respectively (FIG. 1C). However, the addition of an equivalent amount of copper ions in the form of $CuSO_4$ to PPCN resulted in partial gelation at room temperature (FIG. 1D) and the destabilization of the thermoresponsive N isopropylacrylamide groups as no crossover point between G' and G" was detected (FIG. 1C). The lack of an LCST for $PCuSO_4$ is possibly due to strong electrostatic interactions between copper ions and carboxyl groups in PPCN. PPCN, PCMOF and $PCuSO_4$ were incubated at 37° C. in 10% fetal bovine serum (FBS). As shown in FIG. 1E, $PCuSO_4$ broke down into small pieces while PPCN and PCMOF gels remained intact. The higher stability is attributable to the absence of $Cu^{2+}$ and less PPCN crosslinking, which helps PPCN molecules move freely and form more stable gel. The mechanism of sol/gel transition mainly includes hydrophobic interactions, hydrogen bonding, electrostatic interaction, and molecular chain movement (ref 22; herein incorporated by reference in its entirety). For $PCuSO_4$, the interaction between positively charged copper ion and negatively charged carboxylic acid may affect the formation of hydrogen bonds between water molecules and carboxyl groups in the gel. Also, electronic interactions may limit the molecular chain movement of PPCN, which would further influence the hydrophobic interactions between N-isoproylacrylamide monomer (NIPAM) in PPCN (ref 22; herein incorporated by reference in its entirety). For PCMOF, copper ion in CMOF has been coordinated with the carboxyl group of $H_3BTC$, which might resulted in less chance for copper ion to interact with carboxyl group in PPCN and less influence on gel formation, thus contributing to a more stable PCMOF hydrogel.

Figure 1F:
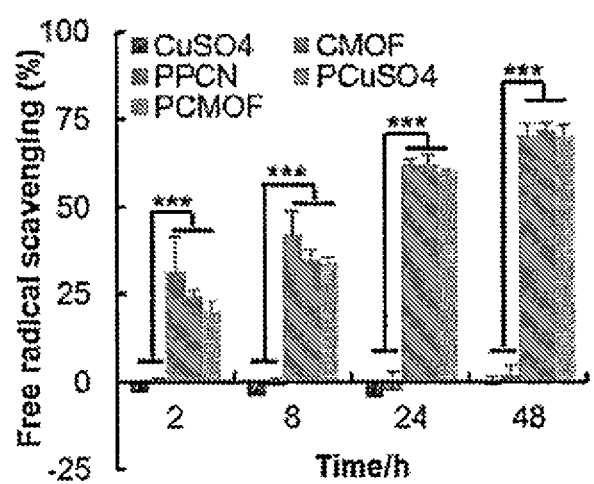

In addition, the ability of PCMOF to scavenge the free radical cation, 2,2'-azino-bis(3-ethylbenzthiazoline-6-sulfonic acid) (ABTS) was assessed. Both PCMOF, $PCuSO_4$ exhibited rapid free radical scavenging activity as per ABTS assay with about 75% of radicals scavenged within 48 hrs, which were similar to that of PPCN, indicating the antioxidant activity of PPCN was reserved after loaded with CMOF or $CuSO_4$. As control, $CuSO_4$, CMOF didn't present a free radical scavenging effect. (FIG. 1F)

PPCN Protects CMOF from Degradation in Fetal Bovine Serum (FBS)

Figure 1G:
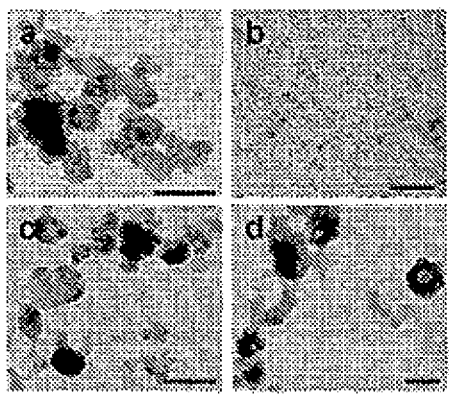
Figure 1H:
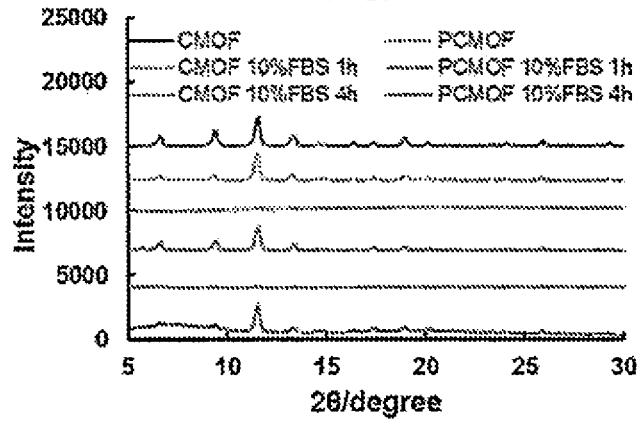

The stability of CMOF alone or dispersed in PPCN gelled at 37° C. before and after incubation in 10% FBS was evaluated using transmission electron microscopy (TEM). CMOF crystals were clearly seen before incubation in FBS and disintegrated after treatment with FBS, confirming that CMOF is not stable in 10% FBS. However, CMOF crystals in PCMOF were observed after treatment with FBS (FIG. 1G), confirming that PPCN protected CMOF from FBS-mediated disintegration.

X-ray diffraction patterns were performed to detect the crystal structure and confirm the TEM study. PCMOF exhibited obvious X-ray diffraction peaks, which were similar to CMOF before treatment with 10% FBS. After treatment with 10% FBS, CMOF peaks disappeared completely for CMOF alone. However, the characteristic peaks from CMOF embedded in PPCN remained present at 4 hrs, further confirming that PPCN is able to stabilize CMOF in protein containing solutions such as FBS.

CMOFs have Reduced Cell Toxicity when Dispersed in PPCN

The cytotoxicity of $CuSO_4$, $PCuSO_4$, CMOF and PCMOF against human epithelial keratinocytes (HEKa) and human dermal fibroblasts (HDF) cells was evaluated by 3-(4,5-dimethylthiazol-2-yl)-2,5-diphenyltetrazolium bromide (MTT) assay. The cytotoxicity of $CuSO_4$ increased with increasing concentrations and no obvious difference was observed after loading into PPCN hydrogel. This is likely due to the fact that $PCuSO_4$ breaks down after adding into the cell culture medium, releasing almost the same amount of copper ion compared to $CuSO_4$ (FIG. 2A, B). The cytotoxicity of CMOF was comparable to that of $CuSO_4$, which may be due to the fact that CMOF was not stable in the cell culture medium and therefore the copper ion release was fast. However, PCMOF showed much lower toxicity against both HEKa and HDF cells, especially at high concentration (1 mmol/L), which may be attributed to the higher stability of CMOF within PPCN and as a result, the sustained release of copper ions from PCMOF. PPCN hydrogel was not toxic to either cell type (FIG. 2C).

Figure 2D:
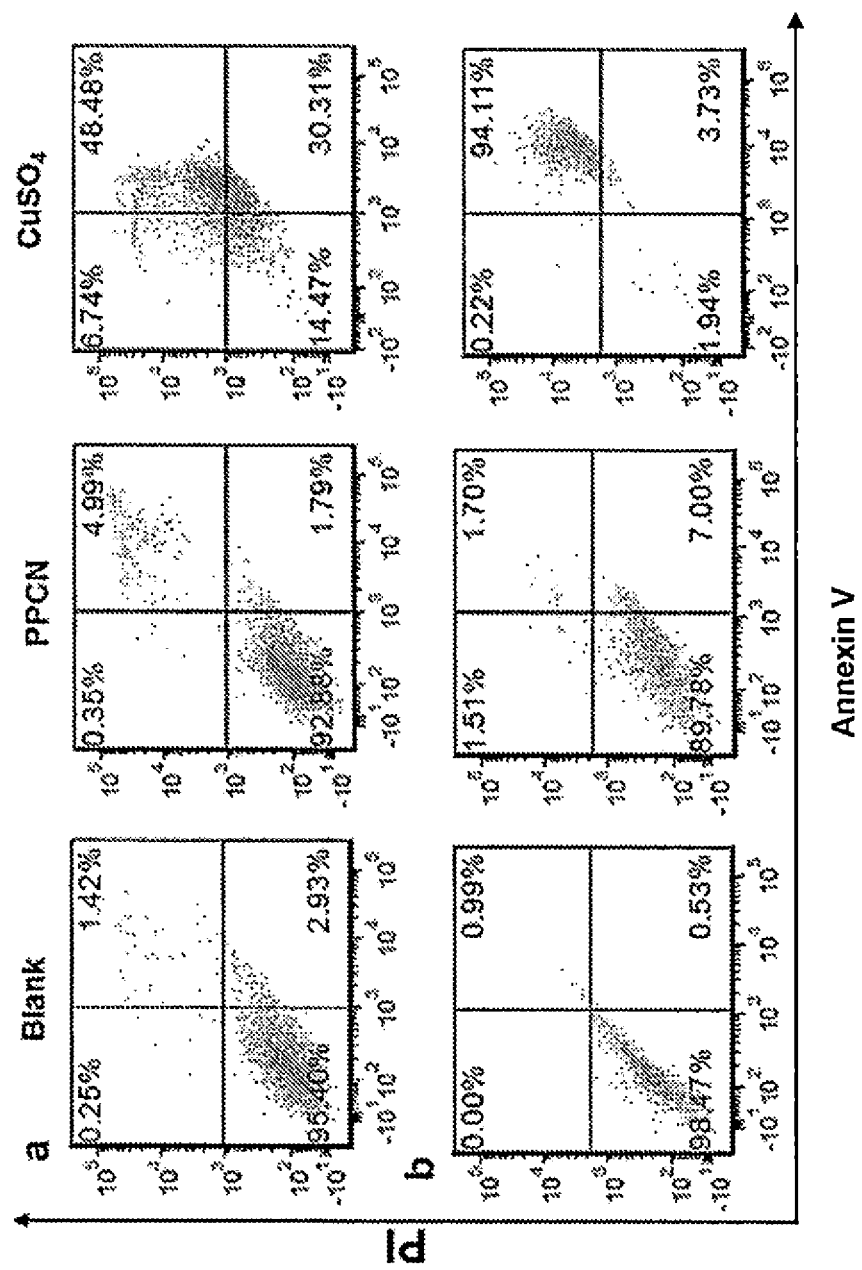
Figure 2E:
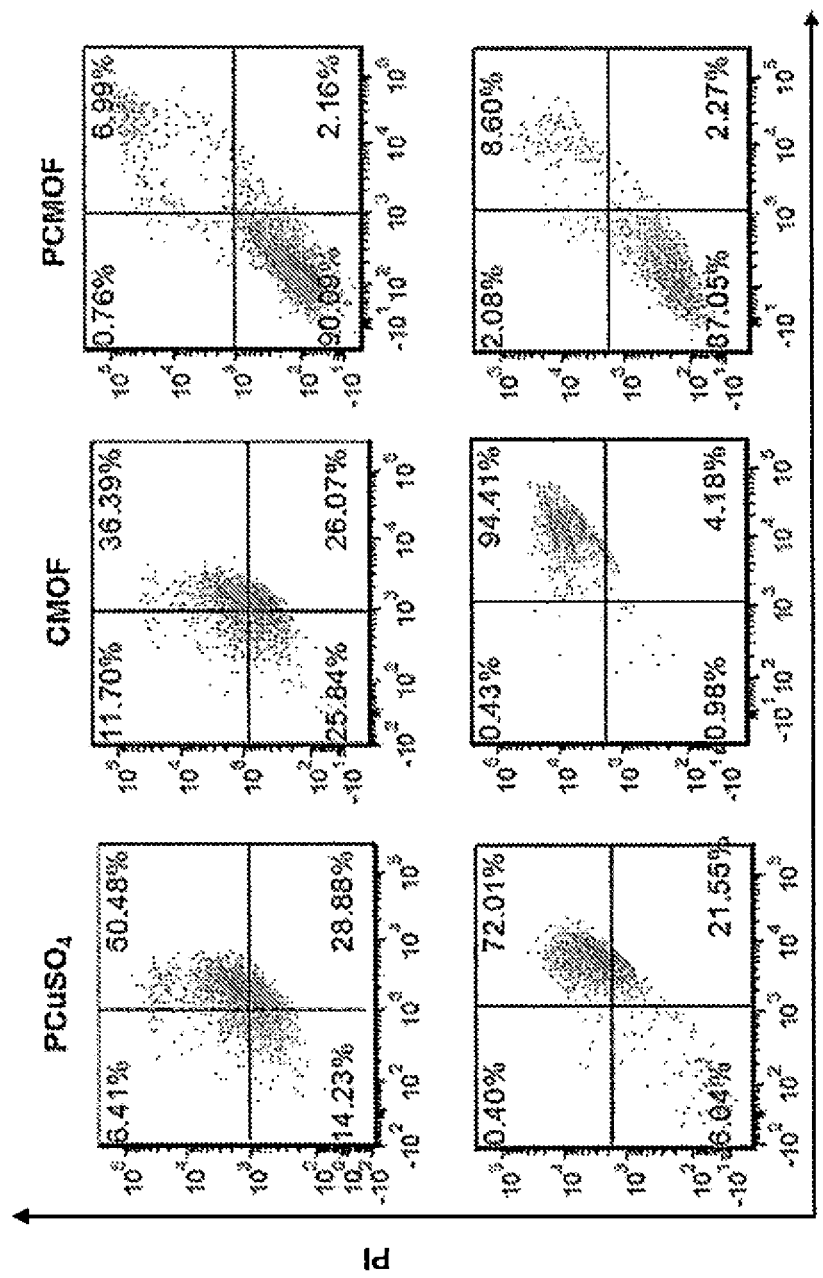

PCMOF does not Induce Cell Apoptosis $CuSO_4$, $PCuSO_4$ and CMOF induced 78.79%, 79.36% and 62.46% cell apoptosis in HEKa cells, and 97.84%, 93.56% and 98.59% cell apoptosis in HDF cells, respectively (FIGS. 2D-E). However, PCMOF only induced 9.15% cell apoptosis in HEKa and 10.87% cell apoptosis in HDF cells. As a reference, PBS induced 4.35% in HEKa cells and 1.52% in HDF cells and PPCN 6.78% in HEKa cells and 8.70% in HDF cells. These results indicate that PCMOF is highly compatible with dermal cells and may be a suitable dressing material for chronic wound healing.

PCMOF Promotes Cell Migration In Vitro

Figure 3A:
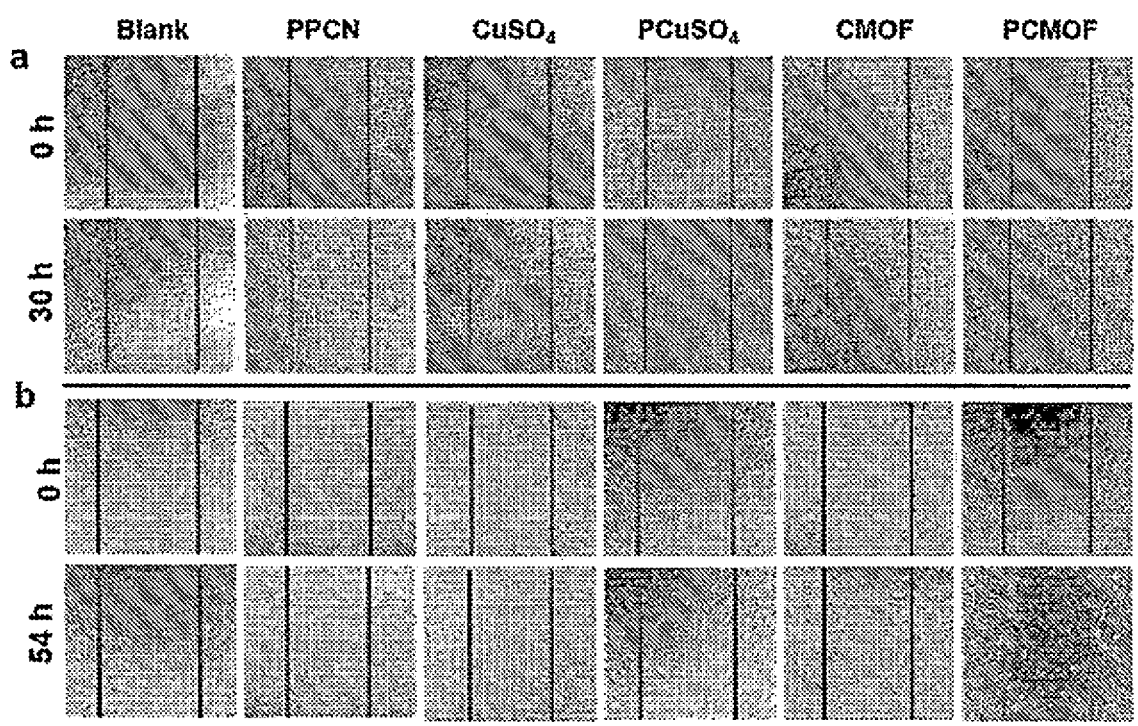
FIGS. 3A-C. Effects of PCMOF on cell migration. A) Photos of (a) HEKa cells and (b) HDF cells after treatment with PPCN, CuSO$_4$, PCuSO$_4$, CMOF, and PCMOF for 0 h and 30 h or 54 h at a concentration of 1×10$^{-3}$ mmol Cu/L. Quantitative analysis of (B) HEKa cell and (C) HDF cell migration after treatment with PPCN, CuSO$_4$, PCuSO$_4$, CMOF, and PCMOF.
Figure 3B:
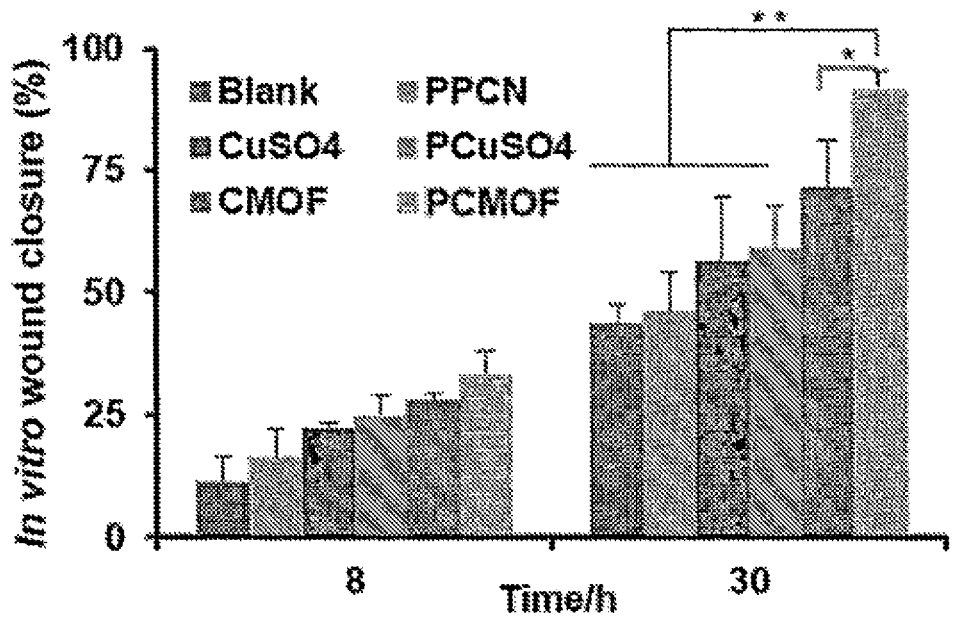
Figure 3C:
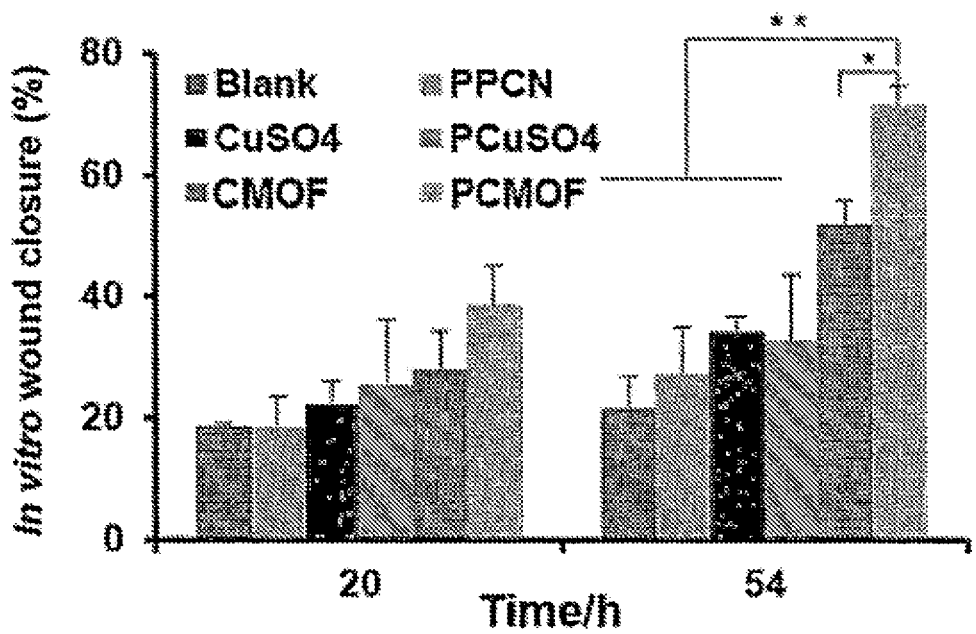

The effect of PPCN, $CuSO_4$, $PCuSO_4$, CMOF and PCMOF on cellular migration over time was measured by a scratch assay (FIG. 3A). For HEKa cells, PPCN showed no effect on the wound closure at 8 h, compared to the blank (cells with no treatment). However, at non cytotoxic concentrations cells in wells exposed to $CuSO_4$ and $PCuSO_4$ showed a significant increase in wound closure and this effect was enhanced in cells that were exposed to CMOF and PCMOF. After incubation for 30 hrs, cells exposed to PCMOF showed the highest wound closure rate (91.69%), followed by those exposed to CMOF (71.67%), $PCuSO_4$ (59.05%), $CuSO_4$ (56.73%), and PPCN (43.76%) (FIG. 3B). HDF cells exposed to PPCN, $CuSO_4$, $PCuSO_4$, CMOF and PCMOF showed similar trends to those observed with HEKa cells. At 54 hrs after treatment, cells exposed to PCMOF exhibited the highest wound closure rate (71.35%), compared to those exposed to CMOF (51.66%), PCuSO$_4$ (32.67%), CuSO$_4$ (34.15%), and PPCN (27.20%) (FIG. 3C).

The increased wound closure rates for cells exposed to CuSO$_4$, PCuSO$_4$, CMOF and PCMOF is due to the presence of copper ion at low concentration without cytotoxicity, which has been reported to stimulate the migration of keratinocytes and fibroblasts through inducing the expression of growth factors VEGF, bFGF and PDGF (ref 23; incorporated by reference in its entirety). The comparable effects of cells exposed to PCuSO$_4$ and CuSO$_4$ on the wound closure rate may be due to the burst release of Cu$^{2+}$. PCMOF promoted the highest rate of cell migration in both cell types, which is attributable to the free radical scavenging activity, lower cytotoxicity, rate of apoptosis and overall improved effects on cellular migration rate.

PCMOF Promotes Dermal Wound Healing in Diabetic Mice

Figure 4A:
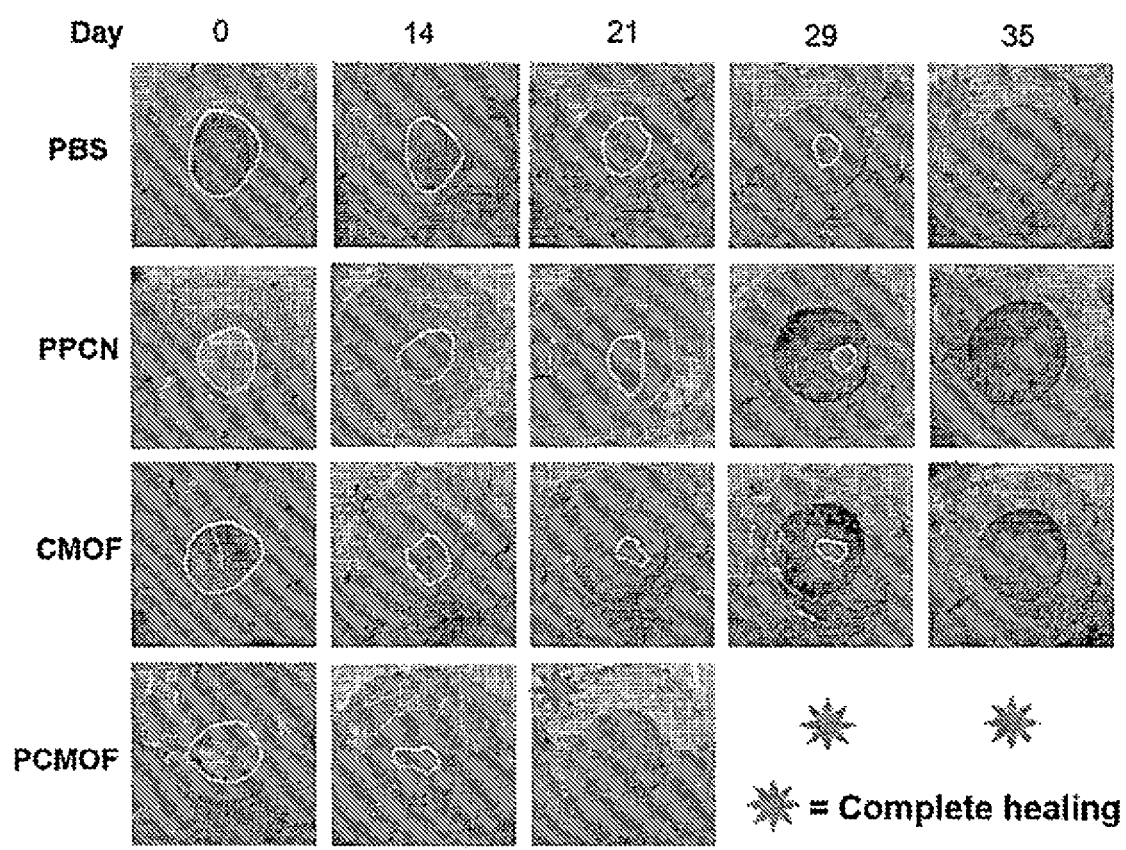

The splinted excisional dermal wound model was used to assess the efficacy and biocompatibility of PCMOF. Each animal received two wounds. Mice were randomly divided into two groups. Animals where one wound was treated with PBS and the other with CMOF and animals where one wound was treated with PPCN and the other with PCMOF. Wounds treated with PCMOF were almost completely healed by day 21 whereas wounds treated with PBS, PPCN, and CMOF healed by day 39, 39 and 37 on average, respectively. (FIG. 4A). The quantitative analysis of digital images of wound closure over time also showed that wound closure rate for PCMOF was significantly higher than PBS, PPCN, and CMOF, especially at day 7, 14, 21, and 29 (FIG. 4B). Wound closure rates for wounds treated with PBS, PPCN and CMOF were similar. The ability of PCMOF to stimulate wound healing in vivo is attributable to the sustained release of copper ions, which induce angiogenesis, collagen deposition and re-epithelialization during wound healing (ref 24; incorporated by reference in its entirety). PCMOF hydrogel may provide an antioxidant moist environment that facilitates wound healing. The low toxicity of PCMOF may also contribute to the increased wound closure rate. The body weight for PPCN and PCMOF-treated mice was constant (FIG. 4C) whereas the body weight for animals treated with PBS and CMOF decreased significantly. These findings further confirm that PPCN and PCMOF are significantly less toxic than CMOF. Interestingly, wounds treated with CMOF showed more wound enlargement than PBS, PPCN and PCMOF at day 4, possibly result from the toxicity of CMOF, which is unstable and release a large number of copper ions within a short time.

PCMOF Promotes Angiogenesis and Collagen Deposition

Diminished peripheral blood flow and decreased local neovascularization are critical factors that contribute to delayed or repair-resistant wounds in diabetics (ref 25; herein incorporated by reference in its entirety), and activation of angiogenesis is required to sustain newly formed granulation tissue (herein incorporated by reference in its entirety). Therefore, the correction of impaired local angiogenesis may be a key component in developing therapeutic protocols for the treatment of chronic wounds of the lower extremities and diabetic foot ulcers (ref 27; herein incorporated by reference in its entirety).

Figures 5A, 5B, 5D:
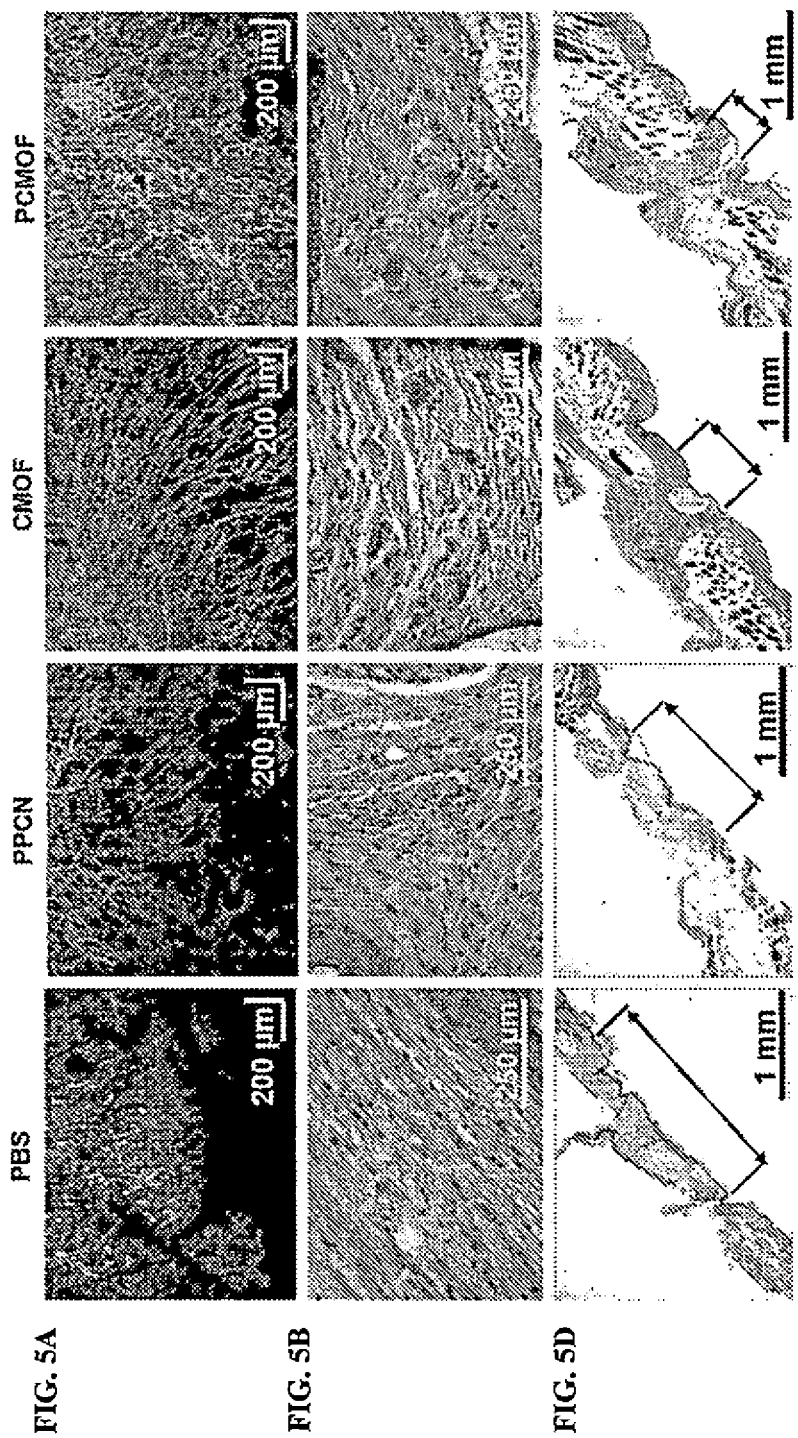
FIGS. 5A-E. Histopathological analysis of healed skin. A) Blood vessels observed by OCT on day 32. B) Blood vessels (arrows) observed after H&E staining. C) Blood vessels density calculated after H&E staining. D) Collagen (light green) of healed skin after Masson's trichrome staining. E) Granulation tissue gap calculated after Masson's trichrome staining.
Figures 5C, 5E:
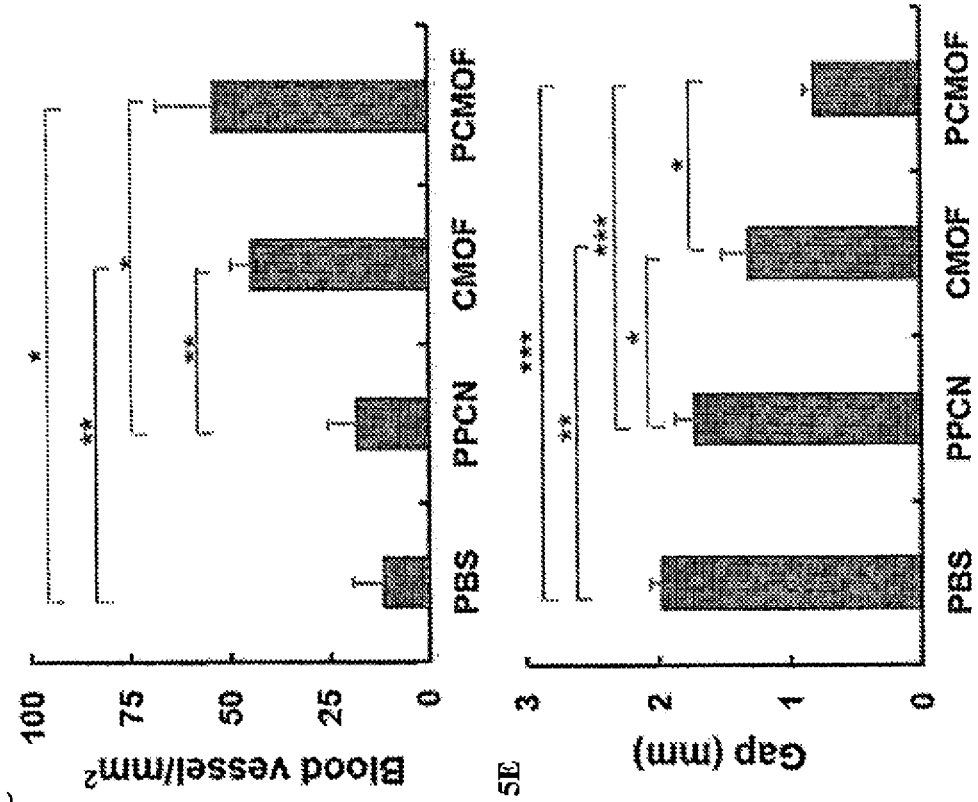

Experiments were conducted to investigate the neovascularization at the site of injury after treatment. Optical coherence tomography (OCT) angiography showed that PCMOF and CMOF were able to promote the formation of a more stable and denser vascular network at the wound site comparing to PBS and PPCN (FIG. 5A). The blood vessels in healed skin were further observed by H&E staining. Neovascularization, including blood vessel number and area, was markedly increased in CMOF- and PCMOF-treated mice (FIG. 5B). Quantitative analysis revealed that the blood vessel number within the granulation tissue was almost 4- and 5-fold higher in CMOF- and PCMOF-treated group than that in PBS-treated group (FIG. 5C). Mean microvessel densities in CMOF- and PCMOF-treated group were 44.4±5.2 and 54.0±14.4 vessels/mm$^2$, respectively, whereas densities in PBS- and PPCN-treated group were only 11.3±8.0 and 18.3±6.9 vessels/mm$^2$, respectively. The ability to stimulate new blood vessel formation could be attributed to the copper ion which has been reported to increase the expression of angiogenic genes, such as VEGF, bFGF and PDGF.[5a] The promotion of angiogenesis could result in a sufficient supply of oxygen and nutrients as well as accelerated migration of the requisite cells and humoral factors into the wounds. These processes, in turn, presumably facilitated the formation of granulation tissue and collagen synthesis, leading to improved wound healing (ref 24; herein incorporated by reference in its entirety).

The synthesis and deposition of collagen is also a critical event to wound healing. As a cofactor to lysyl oxidase, Cu$^{2+}$ stimulates the expression of matrixmetalloproteinase-2 and collagen in fibroblasts, enhancing wound healing (ref 24; herein incorporated by reference in its entirety). Masson's trichrome staining showed much less granulation tissue remaining in the wounds treated with CMOF and PCMOF than that treated with PBS and PPCN (FIG. 5D), indicating CMOF- and PCMOF-treated group exhibited a large improvement in collagen deposition in the granulation tissue. When compared to wounds treated with CMOF, PCMOF-treated group resulted in shorter granulation tissue width, reflecting PCMOF possesses the best effect to promote maturation of granulation tissue and regeneration of epidermis (FIG. 5D, E). HEKa cells, the major cellular component of the epidermis, are important to restoration upon injury through epithelialization (ref 28; herein incorporated by reference in its entirety). PCMOF was able to promote the migration of HEKa cells, which may contribute to the stimulation of re-epithelialization in the chronic wounds. In addition, wounds in a moist environment demonstrate a faster and more direct course of epithelialization (ref 29; herein incorporated by reference in its entirety). PCMOF was able to maintain the humidity of wounds due to the presence of PPCN, which could also contribute to the optimization of re-epithelialization.

Example 3

Folic Acid Stabilized CMOF (CMOF-FA)

CMOF-FA was synthesized by dropwise adding copper acetate monohydrate (0.375 mmol/mL, 1 mL) to H3BTC (0.25 mmol/mL, 0.8-1 mL) and Folic acid (2.5 mg/mL, 0.6-36 mL). The reaction mixture was stirred at room temperature for 40 min to form gel-like light green suspension. The suspension was then centrifuged and the precipitate was washed with DMSO/ethanol/water and ethanol/water (1:1 v/v) twice to obtain purified CMOF-FA.

Figure 6B:
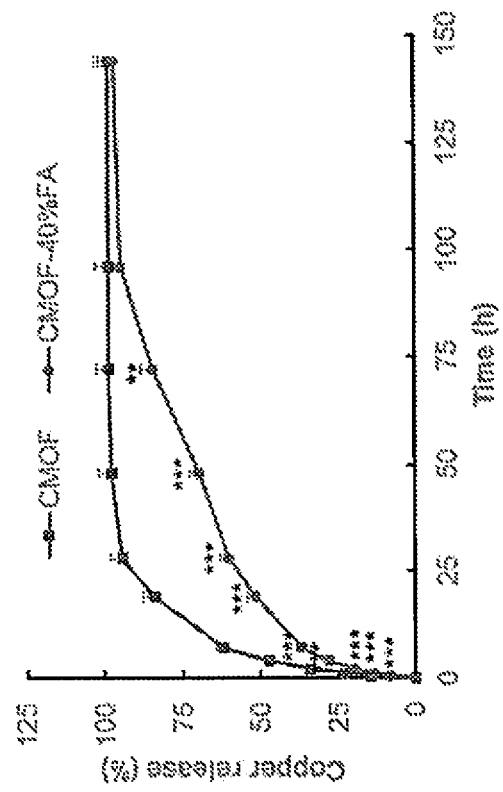
FIGS. 6A-B. Characterization of CMOF-FA. (A) FT-IR spectra of CMOF-FA. (B) Copper release of CMOF-FA.
Figure 6A:
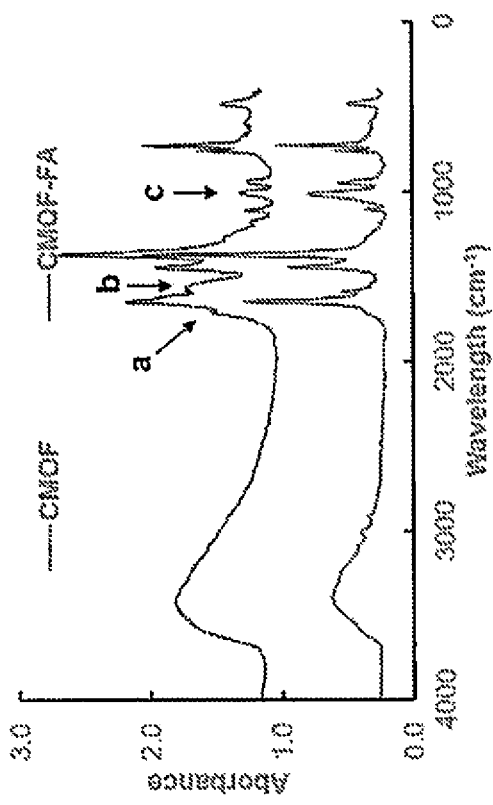

To confirm the success synthesis, Fourier transform infrared (FT-IR) transmission spectra were recorded in attenuated total reflectance mode on a Nicolet Nexus 870 spectrometer (Thermo Scientific, Waltham, Mass.) by accumulation of 32 scans, with a resolution of 8 cm$^{-1}$ (FIG. 6A).

The release of copper from CMOF or CMOF-FA in 5% FBS (pH 7.4, 37° C.) were assessed (FIG. 6B). CMOF or CMOF-FA solution were added into tubes and gently rinsed with 0.1 M PBS (pH 7.4, 37° C.). Samples were incubated in 15 mL 5% FBS and continuously shaken with a speed of 100 rpm at 37° C. At predetermined intervals, all release media was taken out for content measurement and replenished with an equal volume of fresh media at 37° C. The amount of the released copper ion was measured by inductively coupled plasma mass spectrometry (ICP-MS).

Stability of CMOF-FA Against FBS Degradation

CMOF-FA was treated with 10% FBS for 4 h and 24 h, centrifuged for 2 min at the speed of 10,000 rpm, washed twice with ice cold water and resuspended with 50% ethanol. Thereafter, CMOF-FA was dried in vacuum and the crystalline form of CMOF-FA was determined by X-ray diffraction (FIG. 7). CMOF with the same treatment was used as control.

Cytotoxicity Assay

Figure 8:
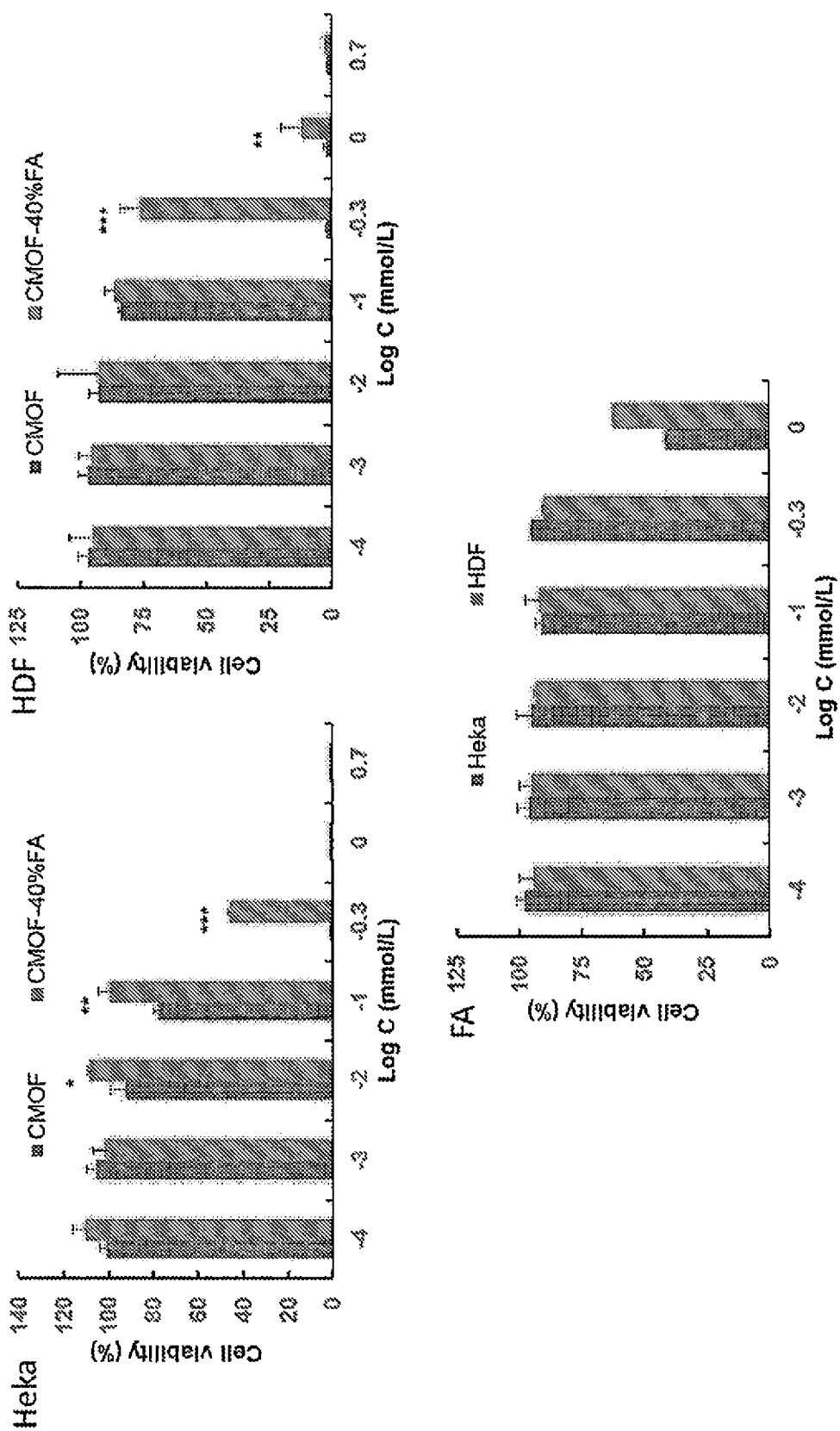
FIG. 8. Cytotoxicity of CMOF-FA on HEKa and HDF cells

HEKa and HDF cells seeded in 96-well plates (5×10$^3$ cells/well) were incubated with a series of concentrations of CMOF, FA and CMOF-FA for 48 h. Then, MTT solution was added to each well to a concentration of 0.5 mg/mL and incubated for an additional 4 h. After that, the medium was removed and 100 μL of dimethyl sulfoxide was added to dissolve crystals formed by living cells. Absorbance at 570 nm was measured using a microplate reader. Cell viability was expressed as a percentage of the absorbance to that of the control experiment without treatment (FIG. 8).

Scratch Assay

Figure 9A:
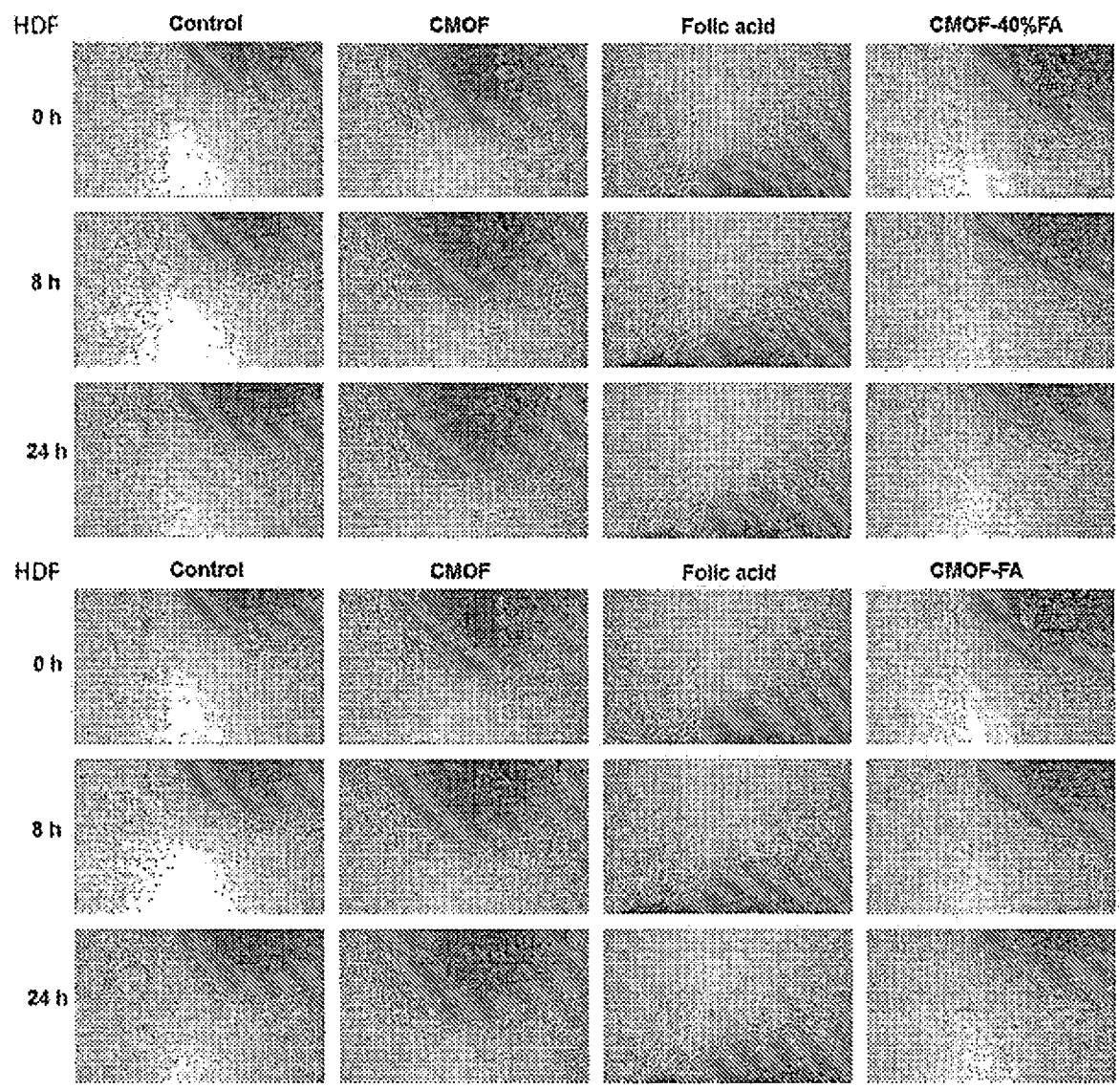
FIGS. 9A-C. Effects of CMOF-FA on cell migration.
Figure 9B:
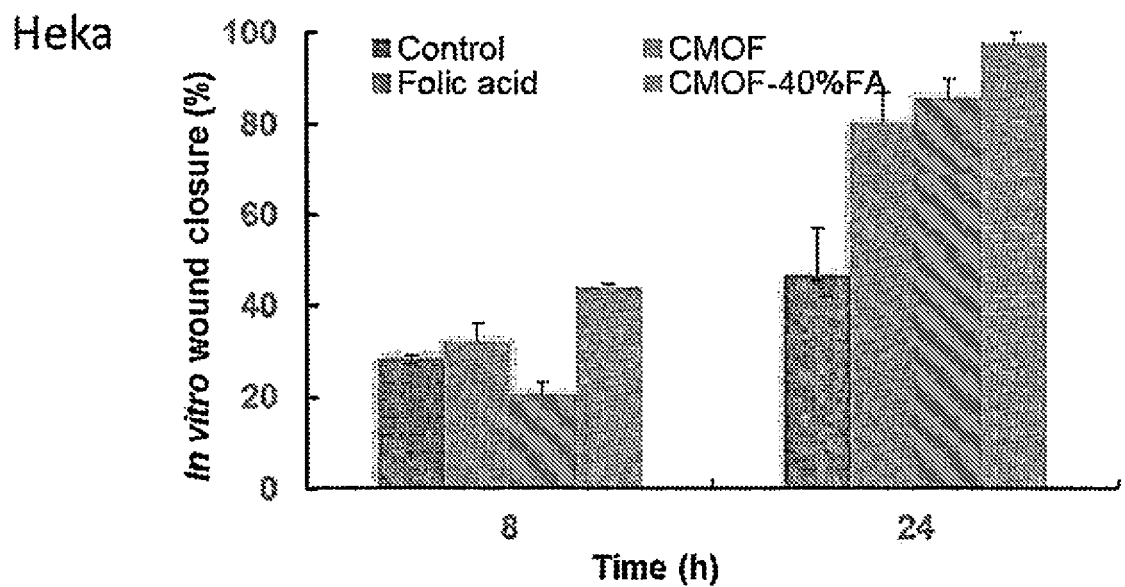
Figure 9C:
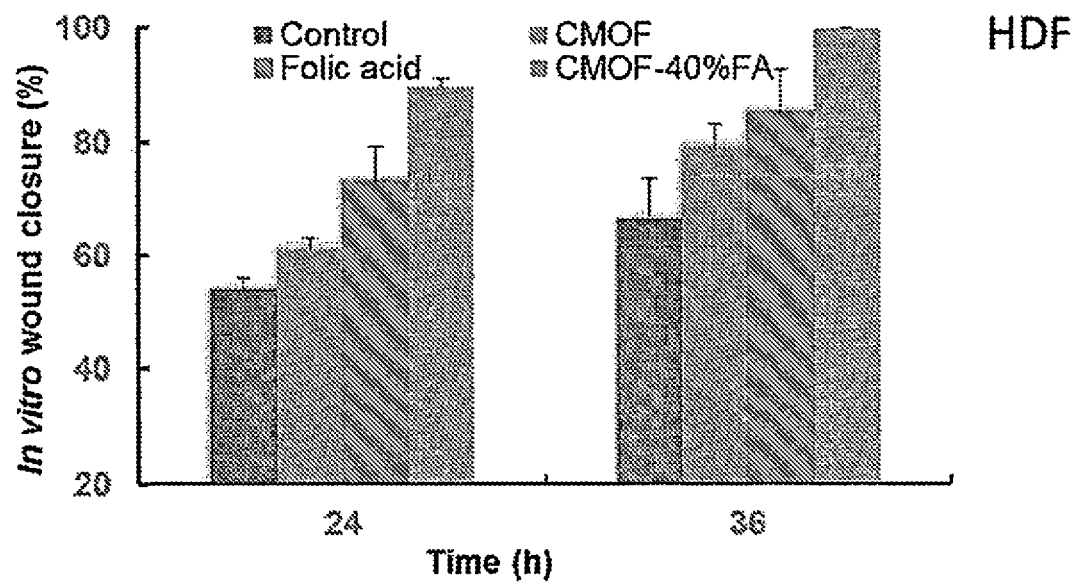

HEKa and HDF cells were seeded in 24-well plates (2×10$^4$ cells/well) and allowed to form a confluent monolayer. After starvation with FBS-free medium, the cell monolayer was scratched in a straightline using 200 μL pipette tip to mimic an incisional wound. Cells were then washed with PBS to remove cell debris and treated with CMOF, folic acid or CMOF-FA (Cu: 1×10$^{-3}$ mmol/L) and incubated at 37° C. with the medium containing 1% FBS for HDF and 5% FBS for HEKa. At desired time intervals, cells were photographed and cell migration rate was calculated (FIGS. 9A-C) using the formula shown as below:

$$\% \text{ wound cloure} = \frac{A0 - At}{A0} \times 100$$

A0: The scratch area at 0 h;

At: The scratch area without cell migration at different time points

Wound Healing In Vivo

Figure 10:
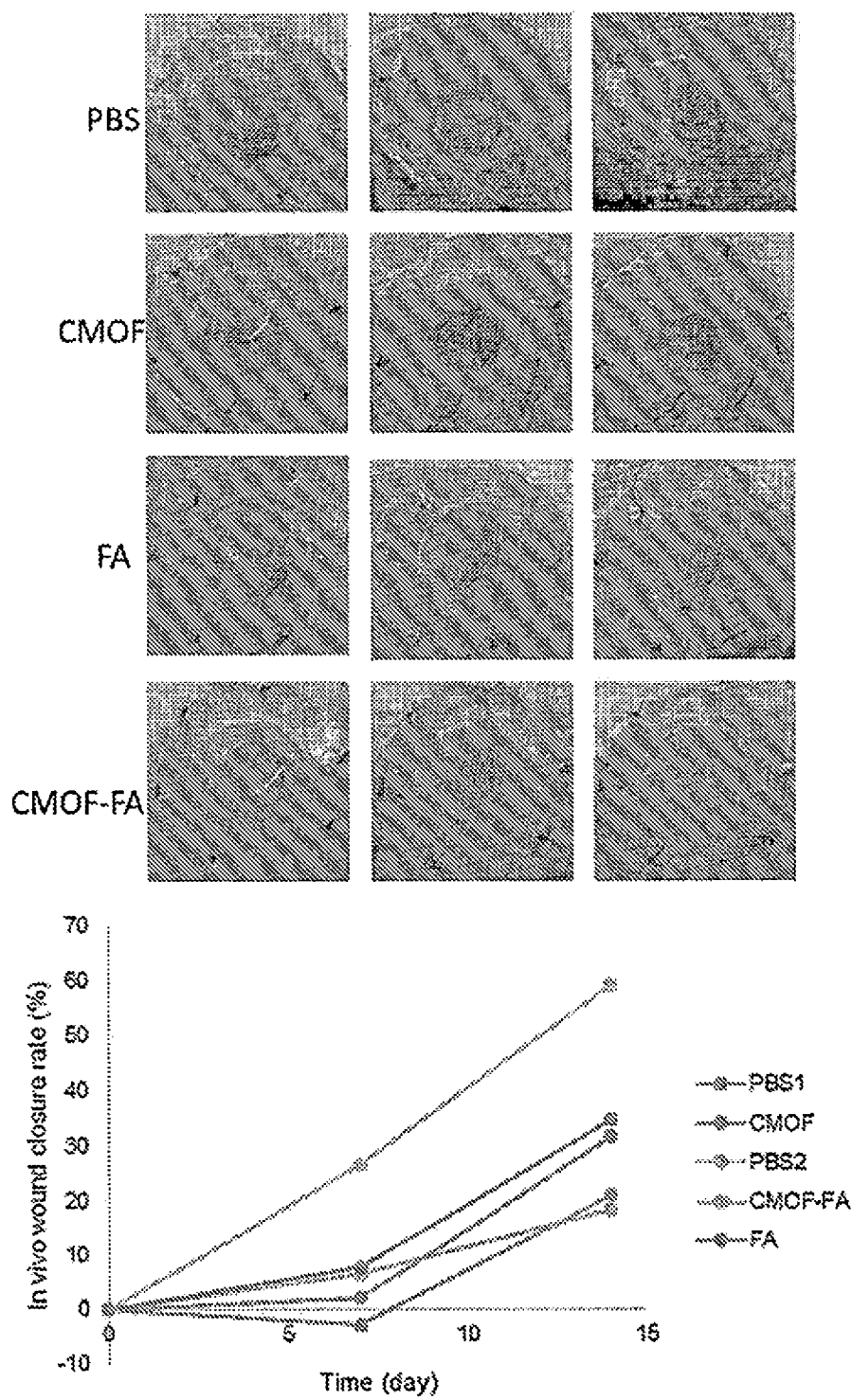
FIG. 10. Effects of CMOF-FA on chronic wound healing in vivo.

Mice (8-10 weeks of age) were anesthetized with isoflurane and the hair on the back of the mice was shaved and completely removed with depilatory cream. After disinfection with betadine and alcohol swabs, mice were subcutaneously injected with buprenorphine (0.5 mg/kg) and two wounds were gently outlined by a marked 6 mm punch biopsy (Acuderm, Fort Lauderdale, Fla.) on each side of the mouse. Following the outline, full-thickness wounds were made using a McPherson-Vannas Micro Scissor (World Precision Instruments, Sarasota, Fla.) and fixed with sterilized and donut-shaped splints. After that, the mice were randomly divided into three groups. Animals where one wound was treated with PBS (40 μL) and the other with CMOF, folic acid or CMOF-FA (Cu: 0.5 mmol/L, 40 μL), respectively. After that, wounds were covered with Tegaderm and coban, animals were individually caged, and formulations were reapplied once a week (FIG. 10).

Tube Formation Assay

Figure 11:
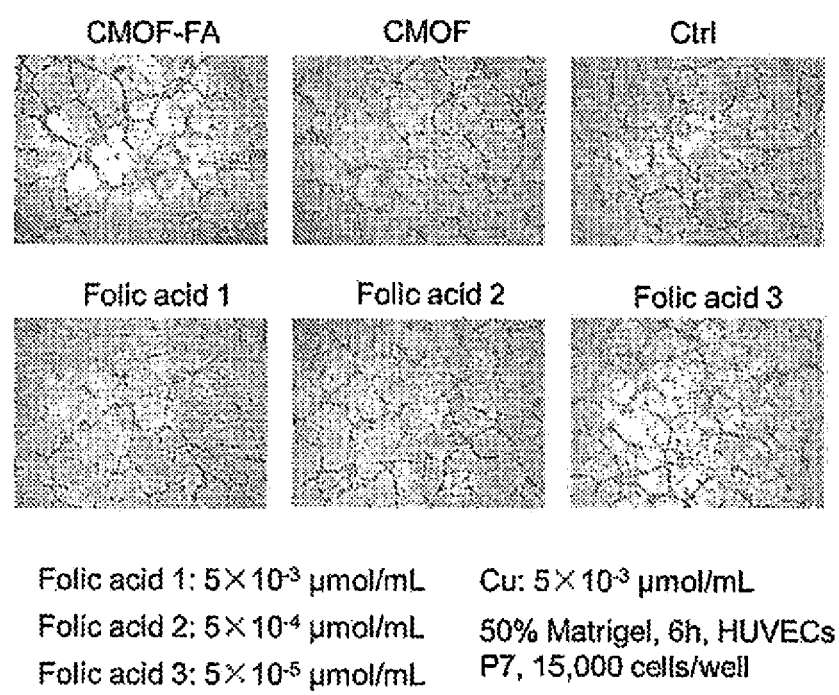
FIG. 11. Effects of CMOF-FA on tube formation.

The tube formation assay was performed to determine the effect of CMOF-FA on angiogenesis in vitro. Briefly, HUVECs cells pretreated with CMOF, folic acid or CMOF-FA were collected and plated on 96-well plates (1.5×10$^4$ cells/well) coated with 50 μL Matrigel (BD Biosciences) and incubated for 6 h. The enclosed networks of complete tubes were photographed (FIG. 11).

Example 4

Thermosensitive CMOF Improves Diabetic Wound Healing

Preparation and Characterization of PPCN-CMOF-Ascorbic Acid Complexes (PCMOFA)

PCMOFA was synthesized by dropwise adding copper acetate monohydrate (0.375 mmol/mL, 0.5 mL) to H3BTC (0.25 mmol/mL, 0.5 mL), ascorbic acid and PPCN (2.5 mg/mL, 2.7 mL, 5.4 mL, 10.8 mL). The reaction mixture was stirred at room temperature for 40 min to form gel-like blue suspension. The suspension was then centrifuged and the precipitate was washed with DMSO/ethanol/water and ethanol/water (1:1 v/v) twice to obtain purified PCMOFA. Also, PPCN-CMOF (PCMOF), CMOF-Ascorbic acid (CMOFA) complexes were synthesized as control.

Figure 12A:
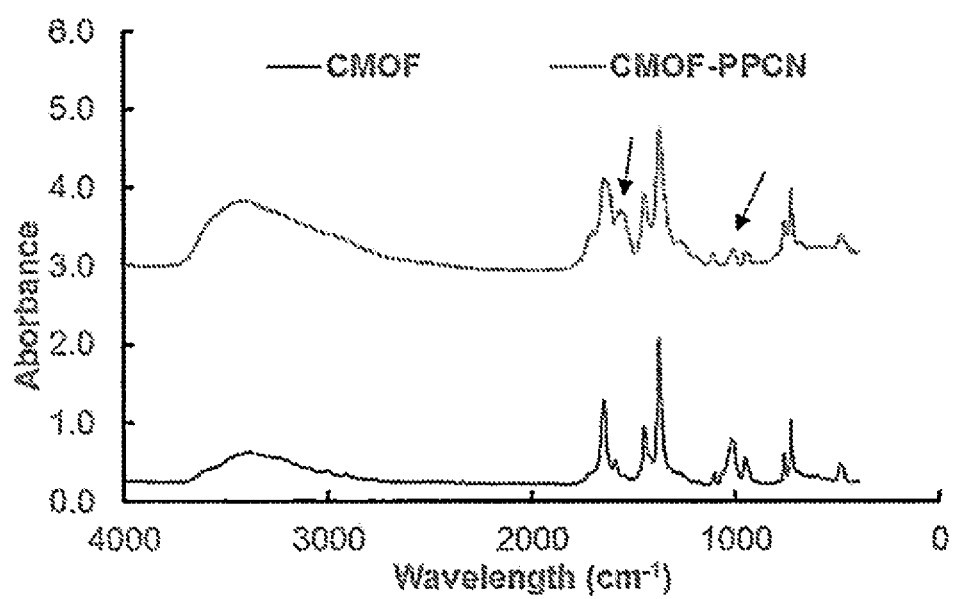
FIGS. 12A-C. Characterization of PCMOFA. (A) FT-IR spectra of PCMOFA. (B) Size of PCMOF at different temperature. (C) Copper release of PCMOFA.

PCMOF sample was dried and Fourier transform infrared (FT-IR) transmission spectra were recorded in attenuated total reflectance mode on a Nicolet Nexus 870 spectrometer (Thermo Scientific, Waltham, Mass.) by accumulation of 32 scans, with a resolution of 8 cm$^{-1}$ (FIG. 12A).

Figure 12B:
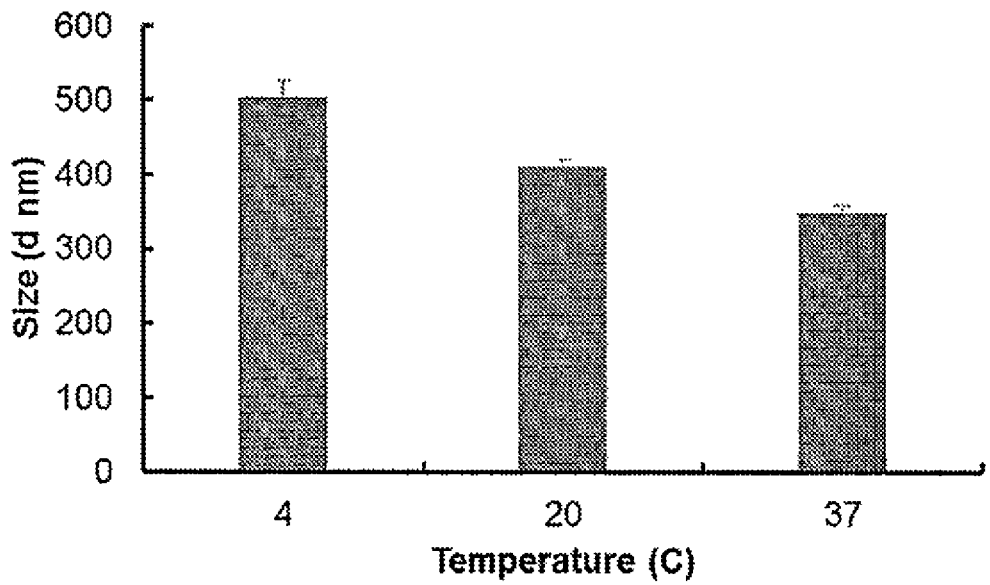

The size of PCMOF suspension at different temperature was determined by Zeta sizer (FIG. 12B).

Figure 12C:
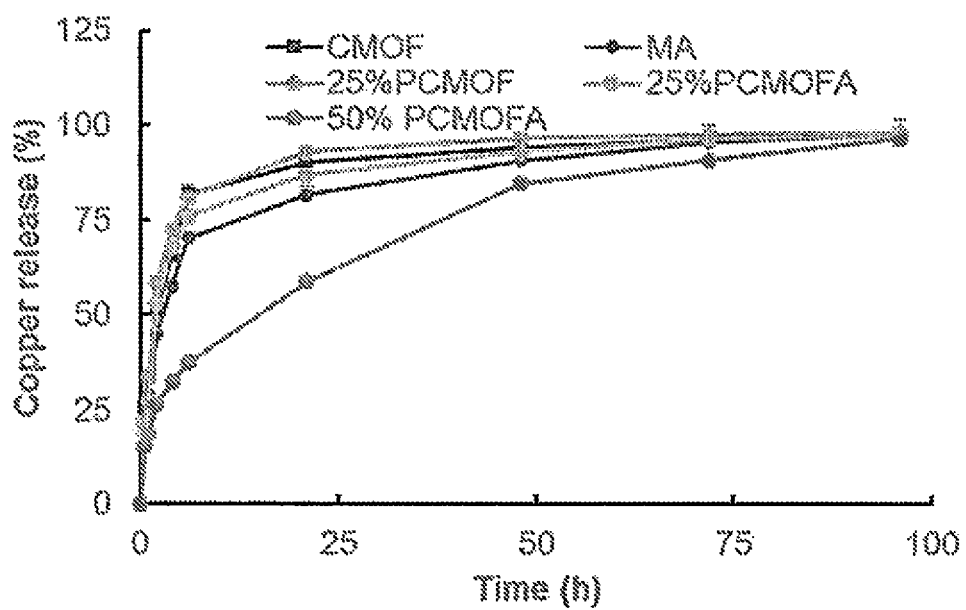

The release of copper from CMOF, CMOFA or PCMOFA in 5% FBS (pH 7.4, 37° C.) were assessed. CMOF or CMOF-FA solution were added into tubes and gently rinsed with 0.1 M PBS (pH 7.4, 37° C.). Samples were incubated in 15 mL 5% FBS and continuously shaken with a speed of 100 rpm at 37° C. At predetermined intervals, all release media was taken out for content measurement and replenished with an equal volume of fresh media at 37° C. The amount of the released copper ion was measured by inductively coupled plasma mass spectrometry (ICP-MS) (FIG. 12C).

Cytotoxicity Assay

Figure 13A:
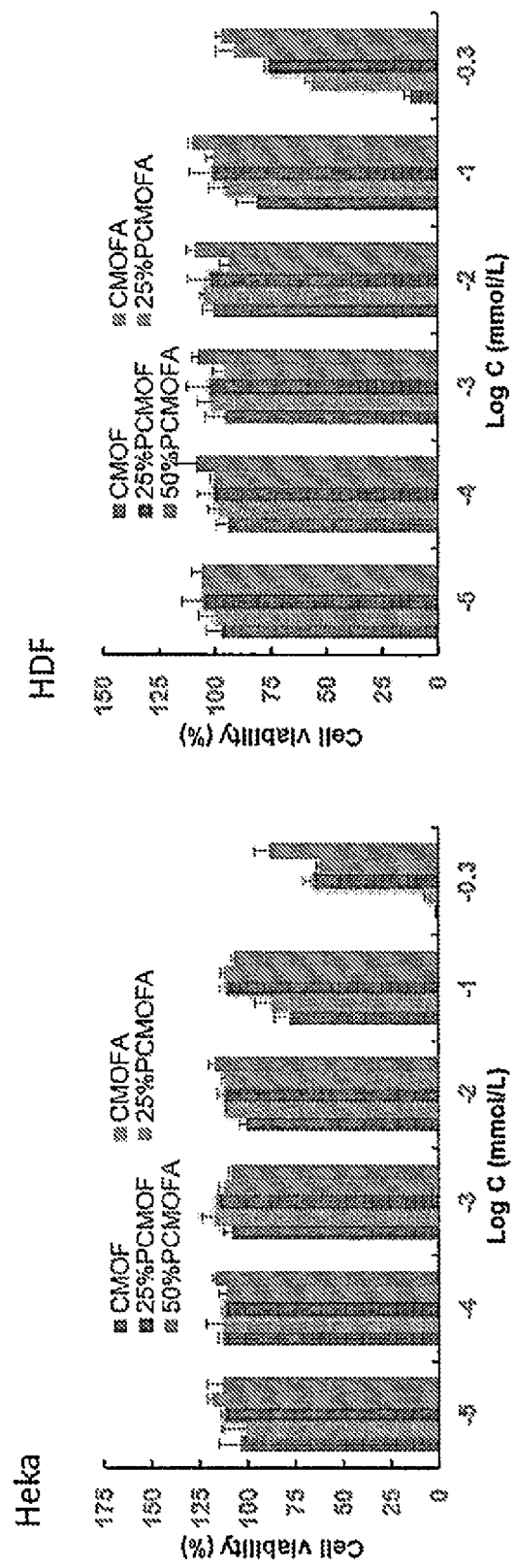
FIGS. 13A-B. Cytotoxicity of PCMOFA on HEKa and HDF cells
Figure 13B:
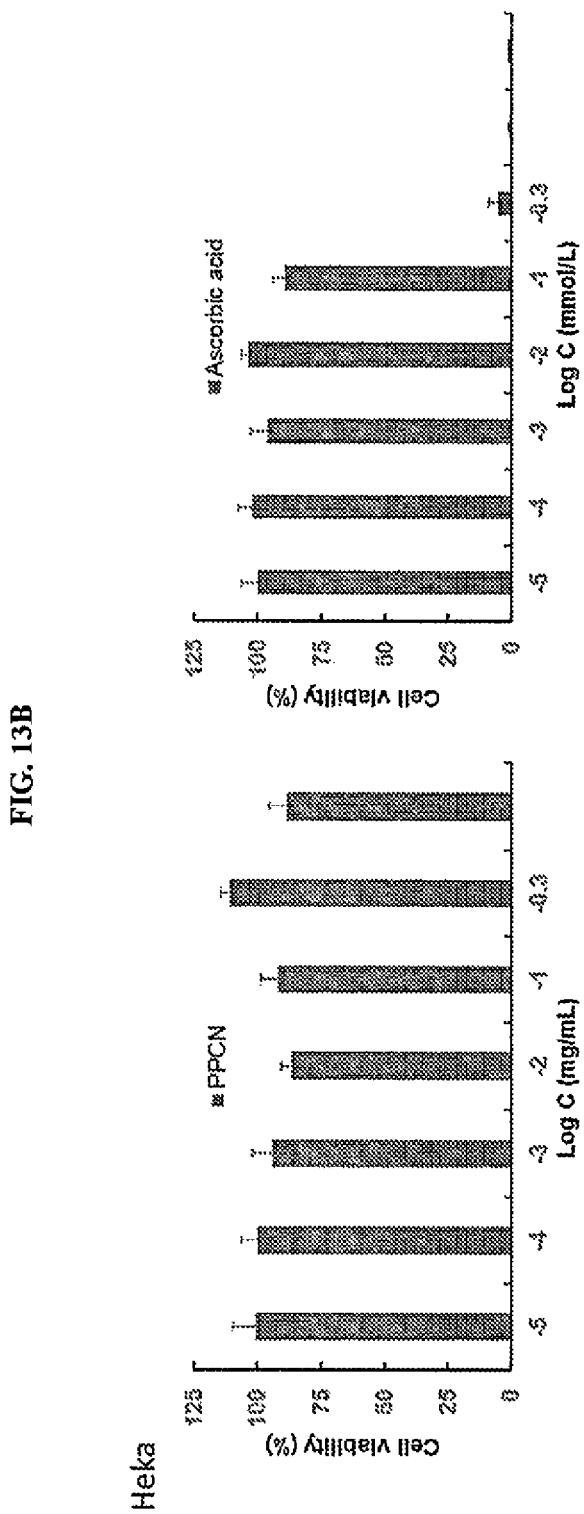

HEKa and HDF cells seeded in 96-well plates (5×10$^3$ cells/well) were incubated with a series of concentrations of PPCN, ascorbic acid, CMOF, CMOFA, 25% PCMOF, 25% PCMOFA and 50% PCMOFA for 48 h. Then, MTT solution was added to each well to a concentration of 0.5 mg/mL and incubated for an additional 4 h. After that, the medium was removed and 100 μL of dimethyl sulfoxide was added to dissolve crystals formed by living cells. Absorbance at 570 nm was measured using a microplate reader. Cell viability was expressed as a percentage of the absorbance to that of the control experiment without treatment (FIGS. 13A-B).

Scratch Assay

Figure 14A:
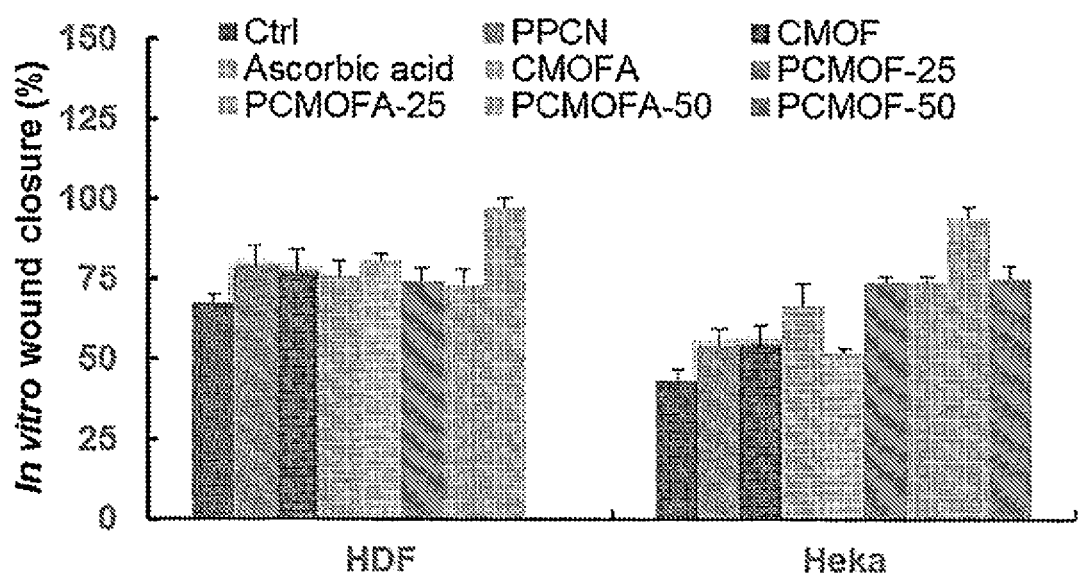
FIGS. 14A-C. Effects of PCMOFA on cell migration.
Figure 14B:
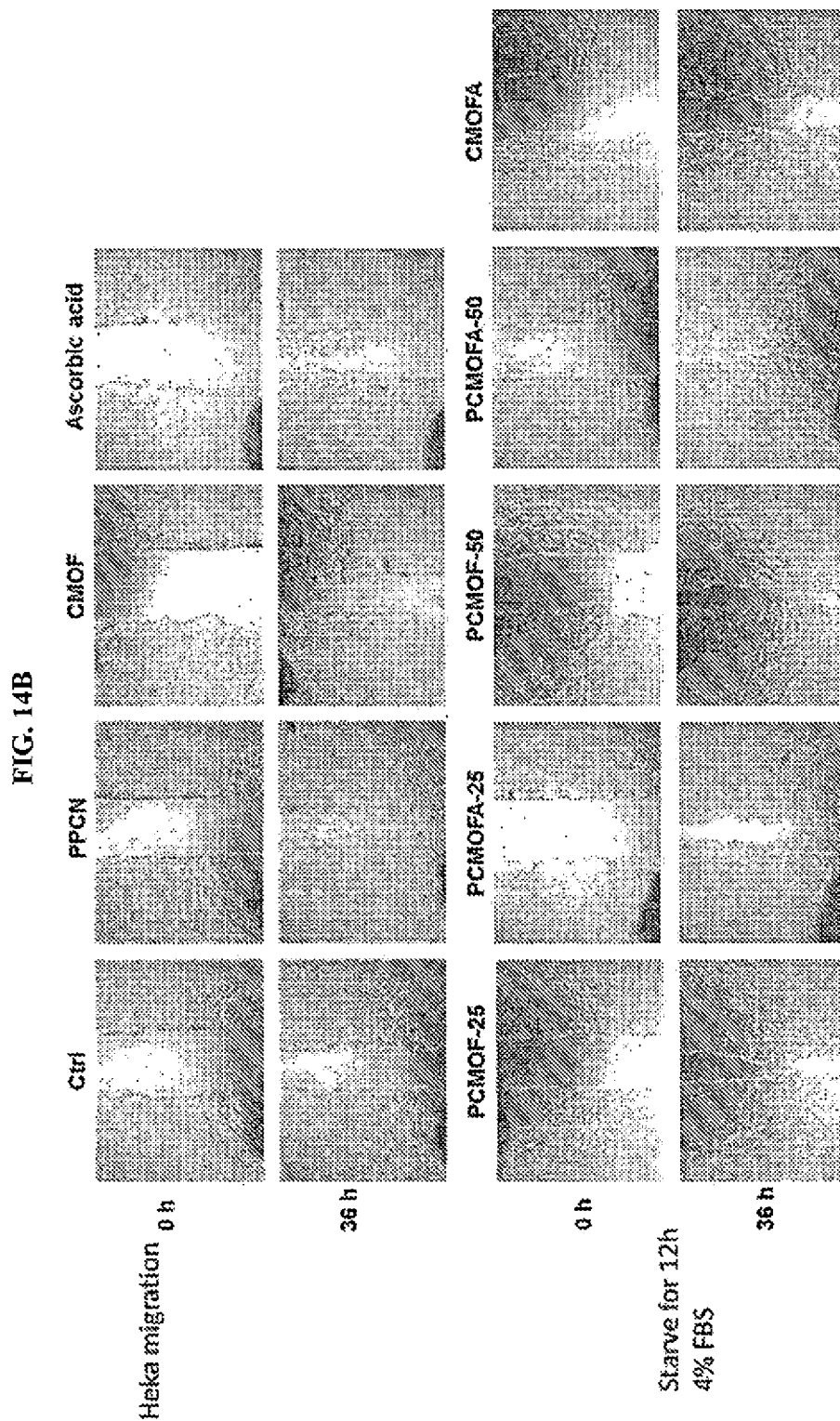
Figure 14C:
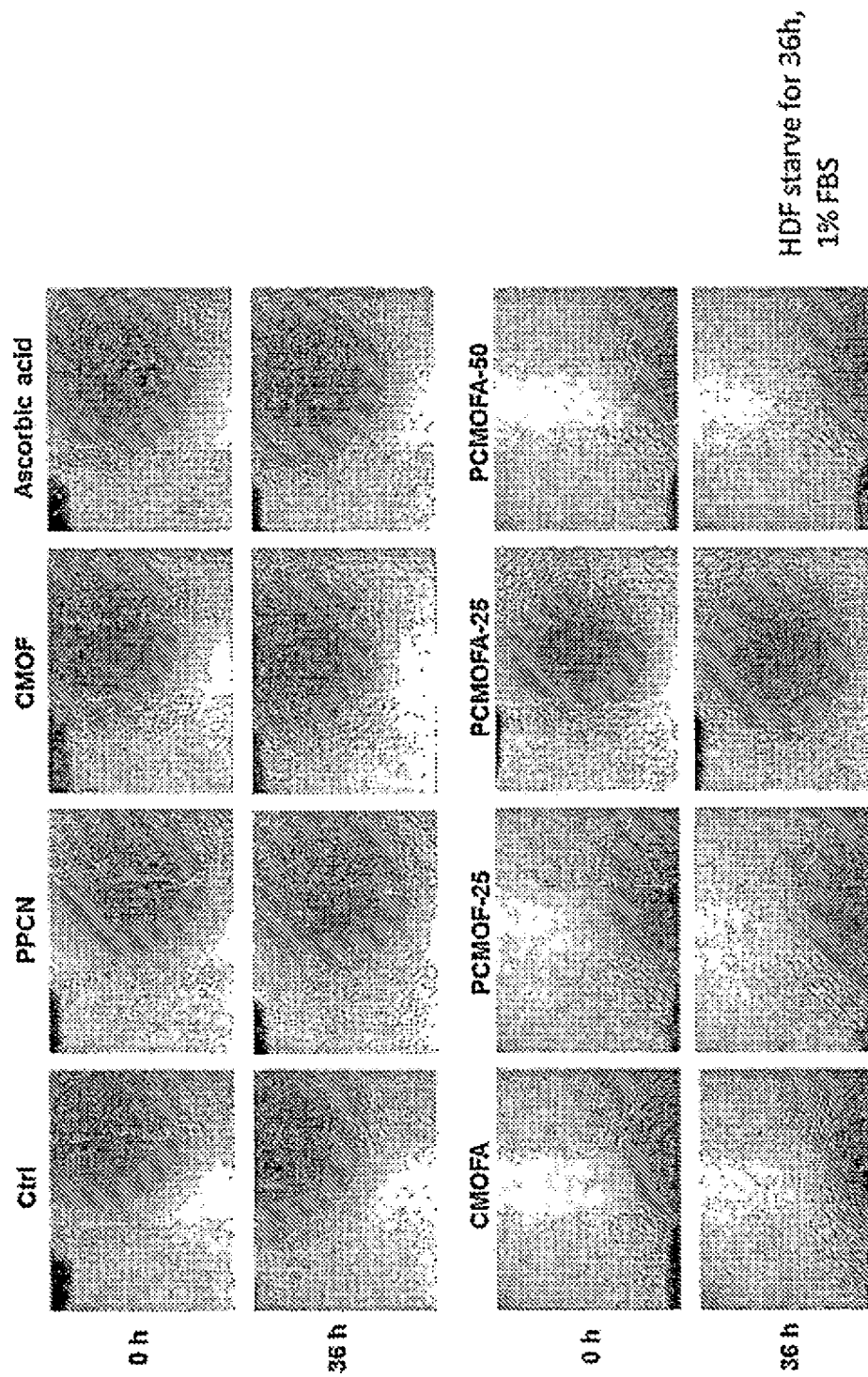

HEKa and HDF cells were seeded in 24-well plates ($2\times10^4$ cells/well) and allowed to form a confluent monolayer. After starvation with FBS-free medium, the cell monolayer was scratched in a straightline using 200 μL pipette tip to mimic an incisional wound. Cells were then washed with PBS to remove cell debris and treated with PPCN, CMOF, ascorbic acid, CMOFA, 25% PCMOF, 25% PCMOFA, 50% PCMOF or 50% PCMOFA (Cu: $1\times10^{-3}$ mmol/L) and incubated at 37° C. with the medium containing 1% FBS for HDF and 4% FBS for HEKa. At desired time intervals, cells were photographed and cell migration rate was calculated (FIGS. 14A-C) using the formula shown as below:

$$\% \text{ wound cloure} = \frac{A0 - At}{A0} \times 100$$

$A0$: The scratch area at 0 h;

$At$: The scratch area without cell migration at different time points

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

REFERENCES

The following references, some of which are cited above, are herein incorporated by reference in their entireties.

[1] a P. S. Randeria, M. A. Seeger, X. Q. Wang, H. Wilson, D. Shipp, C. A. Mirkin, A. S. Paller, Proc. Natl. Acad. Sci. U.S.A. 2015, 112, 5573-5578; b E. J. Mudge, Int. Wound. J. 2015, 12, 4-9; c M. Augustin, K. Herberger, K. Kroeger, K. C. Muenter, L. Goepel, R. Rychlik, Int. Wound J. 2014.

[2] Centers for Disease Control and Prevention. National Diabetes Statistics Report: Estimates of Diabetes and Its Burden in the United States, 2014. Atlanta, Ga.: U.S. Department of Health and Human Services, 2014.

[3] a P. S. Randeria, M. A. Seeger, X. Q. Wang, H. Wilson, D. Shipp, C. A. Mirkin, A. S. Paller, Proc Natl Acad Sci USA 2015, 112, 5573-5578; b Y. Nakamura, H. Ishikawa, K. Kawai, Y. Tabata, S. Suzuki, Biomaterials 2013, 34, 9393-9400.

[4] a M. B. Dreifke, A. A. Jayasuriya, A. C. Jayasuriya, Mater. Sci. Eng. C Mater. Biol. Appl. 2015, 48, 651-662; b A. Nuschke, Organogenesis 2014, 10, 29-37.

[5] a N. Dioufa, A. V. Schally, I. Chatzistamou, E. Moustou, N. L. Block, G. K. Owens, A. G. Papavassiliou, H. Kiaris, Proc. Natl. Acad. Sci. U.S.A. 2010, 107, 18611-18615; b G. Sun, X. Zhang, Y. I. Shen, R. Sebastian, L. E. Dickinson, K. Fox-Talbot, M. Reinblatt, C. Steenbergen, J. W. Harmon, S. Gerecht, Proc. Natl. Acad. Sci. U.S.A. 2011, 108, 20976-20981; c S. Pina, J. M. Oliveira, R. L. Reis, Adv. Mater. 2015, 27, 1143-1169; d L. Loomba, T. Scarabelli, Ther. Deliv. 2013, 4, 1179-1196; e W.-Y. Chen, H.-Y. Chang, J.-K. Lu, Y.-C. Huang, S. G. Harroun, Y.-T. Tseng, Y.-J. Li, C.-C. Huang, H.-T. Chang, Adv. Funct. Mater. 2015, n/a-n/a.

[6] A. Gopal, V. Kant, A. Gopalakrishnan, S. K. Tandan, D. Kumar, Eur. J. Pharmacol. 2014, 731, 8-19.

[7] L. Mandinov, A. Mandinova, S. Kyurkchiev, D. Kyurkchiev, I. Kehayov, V. Kolev, R. Soldi, C. Bagala, E. D. de Muinck, V. Lindner, M. J. Post, M. Simons, S. Bellum, I. Prudovsky, T. Maciag, Proc. Natl. Acad. Sci. U.S.A. 2003, 100, 6700-6705.

[8] a B. Marelli, D. Le Nihouannen, S. A. Hacking, S. Tran, J. Li, M. Murshed, C. J. Doillon, C. E. Ghezzi, Y. L. Zhang, S. N. Nazhat, J. E. Barralet, Biomaterials 2015, 54, 126-135; b J. M. Gillespie, Australas. J. Dermatol. 1973, 14, 127-131.

[9] a T. Amna, M. S. Hassan, J. Yang, M. S. Khil, K. D. Song, J. D. Oh, I. Hwang, Int. J. Nanomedicine 2014, 9, 891-898; b G. Borkow, J. Gabbay, R. Dardik, A. I. Eidelman, Y. Lavie, Y. Grunfeld, S. Ikher, M. Huszar, R. C. Zatcoff, M. Marikovsky, Wound Repair Regen. 2010, 18, 266-275; c C. K. Sen, S. Khanna, M. Venojarvi, P. Trikha, E. C. Ellison, T. K. Hunt, S. Roy, Am. J. Physiol. 2002, 282, H1821-1827.

[10] a L. Guo, I. Panderi, D. D. Yan, K. Szulak, Y. Li, Y. T. Chen, H. Ma, D. B. Niesen, N. Seeram, A. Ahmed, B. Yan, D. Pantazatos, W. Lu, ACS nano 2013, 7, 8780-8793; b N. Hanagata, F. Zhuang, S. Connolly, J. Li, N. Ogawa, M. Xu, ACS nano 2011, 5, 9326-9338.

[11] a J.-L. Zhuang, D. Ceglarek, S. Pethuraj, A. Terfort, Adv. Funct. Mater. 2011, 21, 1442-1447; b G. Majano, O. Martin, M. Hammes, S. Smeets, C. Baerlocher, J. Pérez-Ramírez, Adv. Funct. Mater. 2014, 24, 3837-3837.

[12] W. Lu, Z. Wei, Z. Y. Gu, T. F. Liu, J. Park, J. Park, J. Tian, M. Zhang, Q. Zhang, T. Gentle, 3rd, M. Bosch, H. C. Zhou, Chem. Soc. Rev. 2014, 43, 5561-5593.

[13] J. A. Mason, J. Oktawiec, M. K. Taylor, M. R. Hudson, J. Rodriguez, J. E. Bachman, M. I. Gonzalez, A. Cervellino, A. Guagliardi, C. M. Brown, P. L. Llewellyn, N. Masciocchi, J. R. Long, Nature 2015, 527, 357-361.

[14] W. Zhang, G. Lu, C. Cui, Y. Liu, S. Li, W. Yan, C. Xing, Y. R. Chi, Y. Yang, F. Huo, Adv. Mater. 2014, 26, 4056-4060.

[15] Y. Guo, X. Feng, T. Han, S. Wang, Z. Lin, Y. Dong, B. Wang, J. Am. Chem. Soc. 2014, 136, 15485-15488.

[16] Z. Hu, B. J. Deibert, J. Li, Chem. Soc. Rev. 2014, 43, 5815-5840.

[17] H. Okawa, M. Sadakiyo, T. Yamada, M. Maesato, M. Ohba, H. Kitagawa, J. Am. Chem. Soc. 2013, 135, 2256-2262.

[18] a P. Horcajada, T. Chalati, C. Serre, B. Gillet, C. Sebrie, T. Baati, J. F. Eubank, D. Heurtaux, P. Clayette, C. Kreuz, J.-S. Chang, Y. K. Hwang, V. Marsaud, P.-N. Bones, L. Cynober, S. Gil, G. Ferey, P. Couvreur, R. Gref, Nat. Mater. 2010, 9, 172-178; b B. Atmaja, B. H. Lui, Y. Hu, S. E. Beck, C. W. Frank, J. R. Cochran, Adv. Funct. Mater.

2010, 20, 4091-4097; c V. M. Suresh, S. J. George, T. K. Maji, Adv. Funct. Mater. 2013, 23, 5585-5590; d P. Wu, J. Wang, C. He, X. Zhang, Y. Wang, T. Liu, C. Duan, Adv. Funct. Mater. 2012, 22, 1698-1703; e C. He, D. Liu, W. Lin, Chem. Rev. 2015, 115, 11079-11108.

[19] J. Della Rocca, D. Liu, W. Lin, Acc. Chem. Res. 2011, 44, 957-968.

[20] W. Zhang, Y. Hu, J. Ge, H. L. Jiang, S. H. Yu, J. Am. Chem. Soc. 2014, 136, 16978-16981.

[21] J. Yang, R. van Lith, K. Baler, R. A. Hoshi, G. A. Ameer, Biomacromolecules 2014, 15, 3942-3952.

[22] Y. H. Cheng, S. H. Yang, W. Y. Su, Y. C. Chen, K. C. Yang, W. T. Cheng, S. C. Wu, F. H. Lin, Tissue Eng. Part A 2010, 16, 695-703.

[23] J. E. Sousa, P. W. Serruys, M. A. Costa, Circulation 2003, 107, 2274-2279.

[24] S. Zhao, L. Li, H. Wang, Y. Zhang, X. Cheng, N. Zhou, M. N. Rahaman, Z. Liu, W. Huang, C. Zhang, Biomaterials 2015, 53, 379-391.

[25] Z. J. Liu, O. C. Velazquez, Antioxid. Redox. Signal. 2008, 10, 1869-1882.

[26] T. G. Ebrahimian, F. Pouzoulet, C. Squiban, V. Buard, M. Andre, B. Cousin, P. Gourmelon, M. Benderitter, L. Casteilla, R. Tamarat, Arterioscler. Thromb. Vasc. Biol. 2009, 29, 503-510.

[27] S. A. Eming, P. Martin, M. Tomic-Canic, Sci. Transl. Med. 2014, 6, 265sr266.

[28] I. Pastar, O. Stojadinovic, N. C. Yin, H. Ramirez, A. G. Nusbaum, A. Sawaya, S. B. Patel, L. Khalid, R. R. Isseroff, M. Tomic-Canic, Adv. Wound Care 2014, 3, 445-464.

[29] A. Sood, M. S. Granick, N. L. Tomaselli, Adv. Wound Care 2014, 3, 511-529.

[30] B. Xiao, Q. Yuan, R. A. Williams, Chem. Commun. 2013, 49, 8208-8210.

[31] J. Yi, S. Chen, V. Backman, H. F. Zhang, Biomed. Opt. Express 2014, 5, 3603-3612.

We claim:

1. A composition comprising:
   (a) a metal organic framework (MOF); and
   (b) a polydiolcitrate polyester polymer, wherein the polydiolcitrate comprises poly(polyethyleneglycol citrate-co-N-isopropylacrylamide) (PPCN).

2. The composition of claim 1, wherein the MOF comprises MOF nanoparticles.

3. The composition of claim 1, wherein the MOF comprises transition metal nodes connected by organic ligands.

4. The composition of claim 3, wherein the transition metal is selected from the list consisting of: copper (Cu), zinc (Zn), magnesium (Mg), cobalt (Co), Nickel, (Ni), iron (Fe), manganese (Mn), palladium (Pd), chromium (Cr), lead (Pb), titanium (Ti), and combinations thereof.

5. The composition of claim 3, wherein the organic ligand comprises a molecule selected from the list consisting of: 1,4-di(4'-pyrazolyl)benzene, 1,4,7,10-tetraazacyclododecane-n,n',n",n'"-tetraacetic acid, 2,4,6-(tri-4-pyridinyl)-1,3,5-triazine, tris(isobutylaminoethyl)amine, [1,1'-biphenyl]-4,4'-dicarboxylic acid, 2,5-dihydroxyterephthalic acid, 2,6-naphthalenedicarboxylic acid, 1,4-phenylenediacetic acid, 1,1,2,2-tetra(4-carboxylphenyl)ethylene, 1,3,5-tricarboxybenzene, 1,3,5-tris(4-carboxyphenyl)benzene, and 2-(diphenylphosphino)terephthalic acid.

6. A composition, comprising a composite of:
   (a) copper metal organic framework (CMOF) nanoparticles; and
   (b) a thermoresponsive polydiolcitrate polymer, wherein the polydiolcitrate comprises poly(polyethyleneglycol citrate-co-N-isopropylacrylamide) (PPCN).

7. The composition of claim 6, wherein the CMOF nanoparticles are coated in the thermoresponsive polydiolcitrate polymer.

8. The composition of claim 6, wherein the CMOF nanoparticles are dispersed within the thermoresponsive polydiolcitrate polymer.

9. The composition of claim 6, wherein the CMOF comprises copper metal ion nodes linked by organic ligands selected from the list consisting of: 1,4-di(4'-pyrazolyl)benzene, 1,4,7,10-tetraazacyclododecane-n,n',n",n'"-tetraacetic acid, 2,4,6-(tri-4-pyridinyl)-1,3,5-triazine, tris(isobutylaminoethyl)amine, [1,1'-biphenyl]-4,4'-dicarboxylic acid, 2,5-dihydroxyterephthalic acid, 2,6-naphthalenedicarboxylic acid, 1,4-phenylenediacetic acid, 1,1,2,2-tetra(4-carboxylphenyl)ethylene, 1,3,5-tricarboxybenzene, 1,3,5-tris(4-carboxyphenyl)benzene, and 2-(diphenylphosphino)terephthalic acid.

10. The composition of claim 9, wherein the CMOF comprises copper metal ion nodes linked by 1,3,5-tricarboxybenzene organic ligands.

11. A composition, comprising a composite of:
    (a) copper metal organic framework (CMOF) nanoparticles comprising copper metal ion nodes linked by 1,3,5-tricarboxybenzene organic ligand; and
    (b) poly(polyethyleneglycol citrate-co-N-isopropylacrylamide) (PPCN).

12. The composition of claim 11, wherein the CMOF nanoparticles are coated in the PPCN.

13. The composition of claim 11, wherein the CMOF nanoparticles are dispersed within the PPCN.

14. A method of promoting the healing of a wound comprising administering a composition of one or claim 6 to the wound.

15. A wound dressing comprising a wound-contacting surface, wherein the wound contacting surface comprises a composition of claim 6.

16. The wound dressing of claim 15, wherein the wound dressing comprises a dressing selected from the list consisting of: gauze, a bandage, a film dressing, a pad, and a membrane.

17. A method of treating a wound comprising applying a wound dressing of claim 15.

* * * * *